(12) United States Patent
Katoh et al.

(10) Patent No.: US 12,369,876 B2
(45) Date of Patent: Jul. 29, 2025

(54) FPD NAVIGATION DEVICE AND FPD SYSTEM

(71) Applicant: ASAHI INTECC CO., LTD., Seto (JP)

(72) Inventors: Osamu Katoh, Seto (JP); Kenya Nasu, Seto (JP); Yotaro Nishio, Seto (JP); Kensuke Sakata, Seto (JP); Masahiro Kashiwai, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 250 days.

(21) Appl. No.: 18/198,566

(22) Filed: May 17, 2023

(65) Prior Publication Data

US 2023/0284996 A1 Sep. 14, 2023

Related U.S. Application Data

(63) Continuation of application No. PCT/JP2021/034980, filed on Sep. 24, 2021.

(30) Foreign Application Priority Data

Nov. 19, 2020 (JP) ................. 2020-192772

(51) Int. Cl.
*A61B 6/00* (2024.01)
*A61B 6/42* (2024.01)
*A61B 6/46* (2024.01)
*A61B 6/50* (2024.01)

(52) U.S. Cl.
CPC ............. *A61B 6/54* (2013.01); *A61B 6/4233* (2013.01); *A61B 6/461* (2013.01); *A61B 6/504* (2013.01)

(58) Field of Classification Search
CPC .......... A61B 2018/00404; A61B 34/10; A61B 34/107; A61B 2034/108; A61B 2576/02; A61B 1/00; A61B 5/0033; A61B 5/0035; A61B 5/004; A61B 6/027; A61B 6/03; A61B 6/461; A61B 6/5217; G06T 3/00; G06T 1/00; G06T 3/02; G06T 3/10; G06T 3/14; G06T 3/20; G06T 7/00; G06T 7/60;

(Continued)

(56) References Cited

U.S. PATENT DOCUMENTS 7,725,164 B2   5/2010  Suurmond et al.
2013/0266123 A1  10/2013  Yoshida et al.

FOREIGN PATENT DOCUMENTS

CN    108371547 A  *  8/2018  ........... A61B 6/4411
JP    2013-233413 A    11/2013

* cited by examiner

*Primary Examiner* — Don K Wong
(74) *Attorney, Agent, or Firm* — Oliff PLC

(57) ABSTRACT

A FPD navigation device includes an image acquiring portion that acquires, from a FPD (flat panel detector), a first image including an image of a target blood vessel taken at a first position, and a second image including an image of the target blood vessel taken at a second position different from the first position; a position information acquiring portion that acquires position information on the target blood vessel from the first image, the second image, position information on the first position, and position information on the second position; and a recommendation range output portion that outputs, from the position information on the target blood vessel, a FPD imaging position recommendation range representing a range of an imaging position of the FPD recommended for acquiring an image of the target blood vessel.

23 Claims, 19 Drawing Sheets

(58) Field of Classification Search
CPC ... G06T 7/70; G06T 7/97; G06T 2207/10132; G06T 2207/10116
See application file for complete search history.

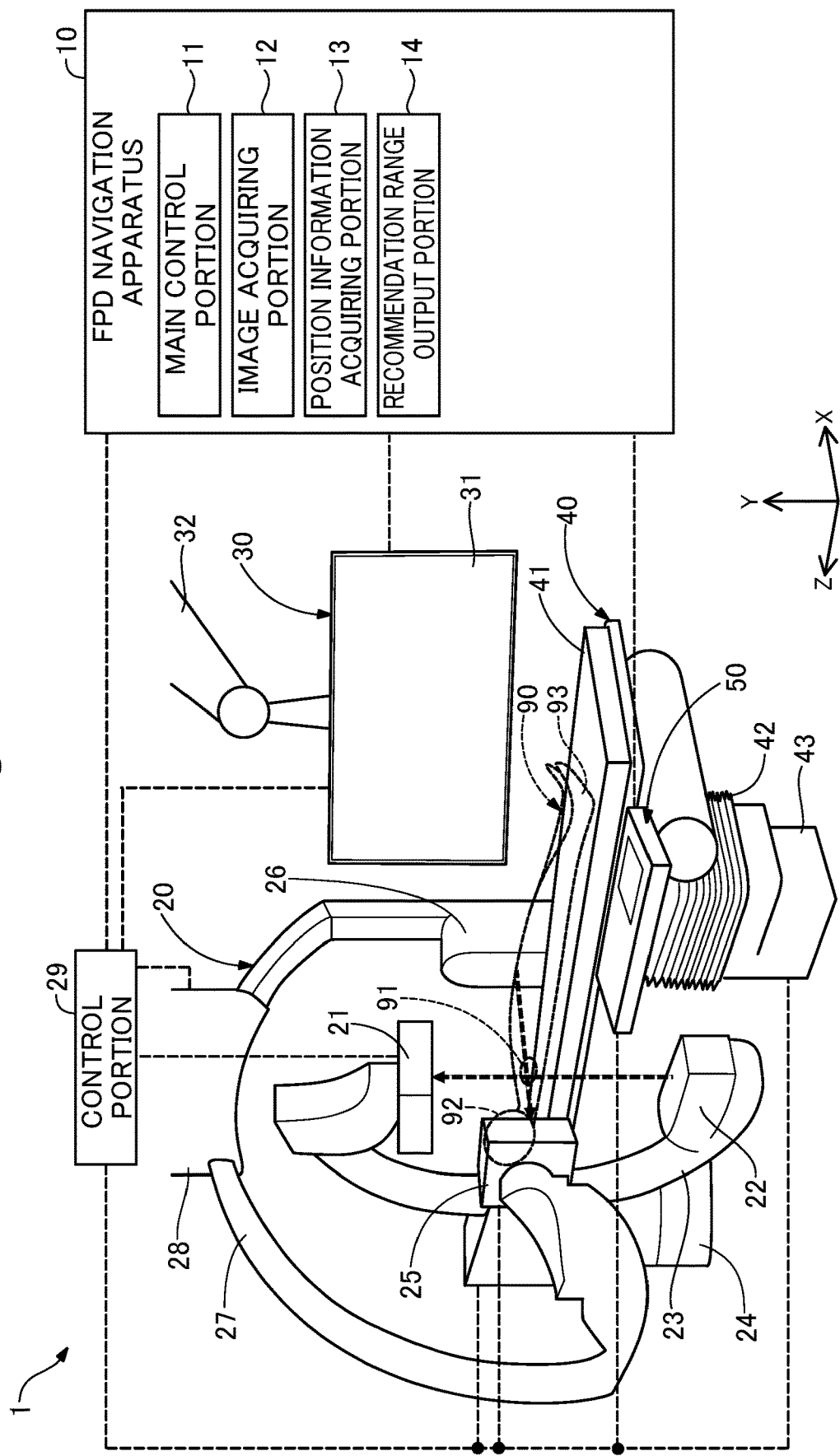

LAO

RAO

CRA

CAU

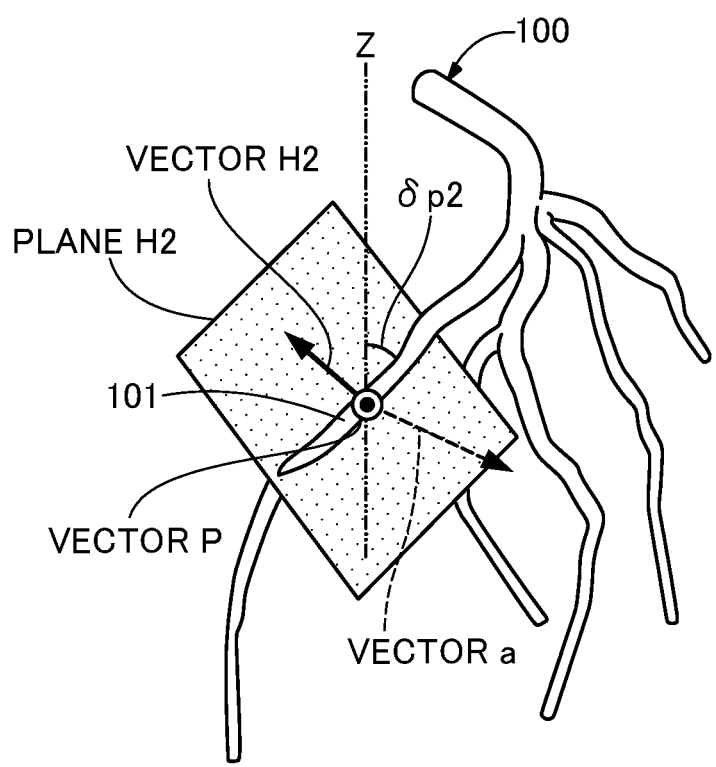

FPD NAVIGATION DEVICE AND FPD SYSTEM

This application is a Bypass Continuation of International Application No. PCT/JP2021/034980 filed Sep. 24, 2021, which is based upon and claims the benefit of priority from Japanese Patent Application No. 2020-192772 filed Nov. 19, 2020, the entire contents of the prior applications being incorporated herein by reference.

TECHNICAL FIELD

The present disclosure relates to a FPD navigation device and a FPD system.

BACKGROUND ART

In recent years, a FPD (flat panel detector) has been used in blood vessel imaging conducted for examination or therapy. A FPD is a device that takes an image by harvesting X-rays transmitted through a human body and converting them into a digital signal. Such a FPD enables achieving a higher-definition image quality, and also has the advantages of a more compressed time to image display and a lower exposure level, compared to conventional CR (computed radiography) systems. For example, Patent Literature 1 discloses the creation of a synthetic view of a segment of interest of a technician, from image data produced in an X-ray imaging apparatus such as a FPD.

CITATION LIST

Patent Literature

Patent Literature 1: U.S. Pat. No. 7,725,164

SUMMARY

Technical Problem

A technician uses a FPD to take an image of a blood vessel to be targeted for examination or therapy (hereinafter also referred to as a target blood vessel), and manipulates a medical device, such as a guidewire, inserted into a blood vessel, along with checking a position of each of a blood vessel, a lesion, and the medical device included in the image. This causes a problem in that when an imaging position of a FPD (i.e., a position of a FPD relative to a target blood vessel) is not appropriate, a technician cannot correctly know a positional relation among a blood vessel, a lesion, and a medical device, and thus cannot push and advance a medical device in an intended direction. In the case of closure inside a blood vessel due to a lesion, such as chronic total occlusion (CTO), the aforementioned problem has been particularly prominent in a subintimal approach to re-insert a medical device from a false lumen to a true lumen for opening of the CTO (re-opening).

In this regard, the system in Patent Literature 1 is only described as generating a synthetic view from a blood vessel image previously acquired, and has not taken into account introduction of a FPD to an appropriate imaging position at all. Such a problem lies commonly in performing X-ray imaging with use of a FPD, not only for a blood vessel system, but also for a biological lumen such as a lymph gland system, a biliary tract system, a urinary tract system, a respiratory tract system, a digestive organ system, a secretory gland, or a genital organ.

The present disclosure was made for solving at least a part of the aforementioned problems, and has as an object to guide an imaging position of a FPD recommended for acquiring an image of a target blood vessel.

Solution to Problem

The present disclosure was made for solving at least a part of the aforementioned problems, and can be achieved in the following aspects.

(1) An aspect in the present disclosure provides a FPD navigation device. The FPD navigation device includes an image acquiring portion that acquires, from a FPD (flat panel detector), a first image including an image of a target blood vessel taken at a first position, and a second image including an image of the target blood vessel taken at a second position different from the first position; a position information acquiring portion that acquires position information on the target blood vessel from the first image, the second image, position information on the first position, and position information on the second position; and a recommendation range output portion that outputs, from the position information on the target blood vessel, a FPD imaging position recommendation range representing a range of an imaging position of the FPD recommended for acquiring an image of the target blood vessel.

According to this configuration, the position information acquiring portion is capable of acquiring position information on the target blood vessel, using the first image and the second image taken at two different imaging positions (first position and second position), position information on the first position, and position information on the second position. Moreover, the recommendation range output portion derives a FPD imaging position recommendation range (a range of an imaging position of a FPD recommended for acquiring an image of the target blood vessel) using the position information on the target blood vessel thus obtained, and outputs the FPD imaging position recommendation range. A technician sets an imaging position of the FPD so as to overlap the FPD imaging position recommendation range thus output, and thereby can guide the FPD to an appropriate imaging position. The technician performs a procedure with checking the taken image of the FPD obtained in this manner (an image of the target blood vessel), and thereby can correctly know a positional relation among a blood vessel, a lesion, and a medical device, and push and advance the medical device in an intended direction. Consequently, the configuration enables guidance of an imaging position of a FPD recommended for acquiring an image of a target blood vessel.

(2) In the FPD navigation device according to the aforementioned aspect, the recommendation range output portion may make the display portion display a guide screen including an image indicating the FPD imaging position recommendation range.

According to this configuration, the recommendation range output portion makes the display portion display a guide screen including an image indicating the FPD imaging position recommendation range, and thus a technician can check the guide screen displayed on a display portion, and thereby identify the FPD imaging position recommendation range with ease.

(3) In the FPD navigation device according to the aforementioned aspect, the recommendation range output portion in imaging the target blood vessel at a plurality of imaging positions by the FPD may make the guide screen displayed upon identification of a first imaging position, wherein the guide screen includes a second imaging-range image indicating a range of an imaging position of the FPD recommended as a second imaging position.

According to this configuration, the recommendation range output portion in imaging the target blood vessel at a plurality of imaging positions by the FPD makes the guide screen displayed upon identification of a first imaging position, wherein the guide screen includes a second imaging-range image indicating a range of an imaging position of the FPD recommended as a second imaging position. Thus, for example, a blood vessel imaging apparatus including two FPDs capable of simultaneous bidirectional imaging such as in a vertical direction (longitudinal direction) and a normal direction (lateral direction) enables guidance of a FPD imaging position recommendation range for each of the FPD.

(4) In the FPD navigation device according to the aforementioned aspect, the recommendation range output portion may make the guide screen displayed, the guide screen having a first screen including a first imaging-range image indicating a range of an imaging position of the FPD recommended as the first imaging position and a second screen including the second imaging-range image, and may change the second imaging-range image in the second screen corresponding to the first imaging position determined from the first imaging-range image in the first screen.

According to this configuration, the recommendation range output portion makes the guide screen displayed, the guide screen having a first screen including a first imaging-range image for a first imaging position and a second screen including a second imaging-range image for a second imaging position, and thus a technician can know a FPD imaging position recommendation range for each FPD with ease. The recommendation range output portion also changes the second imaging-range image in the second screen corresponding to the first imaging position determined from the first imaging-range image in the first screen; thus, for example, a blood vessel imaging apparatus including two FPDs capable of simultaneous bidirectional imaging such as in a vertical direction (longitudinal direction) and a normal direction (lateral direction) enables more appropriate guidance of a FPD imaging position recommendation range for each of the FPD.

(5) In the FPD navigation device according to the aforementioned aspect, and within the guide screen, the first imaging-range image in the first screen may be indicated as a part having intersection of a range of an imaging position of the FPD in a direction perpendicular to an extending direction of the target blood vessel and a motion range of the FPD, and the second imaging-range image in the second screen may be indicated as a predetermined range including an imaging position of the FPD in a second imaging direction perpendicular to a first imaging direction in a specified imaging position of the FPD in the first screen.

According to this configuration, in the guide screen, the first imaging-range image in the first screen is indicated as a part having intersection of a range of an imaging position of the FPD in a direction perpendicular to an extending direction of the target blood vessel and a motion range of the FPD. Thus, the first imaging-range image in the first screen can be used to guide a FPD imaging position recommendation range in a vertical direction (longitudinal direction). Furthermore, in guide screen, the second imaging-range image in the second screen is indicated as a predetermined range including an imaging position of the FPD in a second imaging direction perpendicular to a first imaging direction in a specified imaging position of the FPD in the first screen. Thus, the second imaging-range image in the second screen can be used to guide a FPD imaging position recommendation range in a normal direction (lateral direction).

(6) In the FPD navigation device according to the aforementioned aspect, the guide screen may further have a third screen including a third imaging-range image indicating a range of an imaging position of the FPD recommended as an imaging position from a third imaging direction in a direction perpendicular to the first imaging direction and opposite to the second imaging direction, in addition to the first screen and the second screen.

According to this configuration, the guide screen further has a third screen including a third imaging-range image indicating a range of an imaging position of the FPD recommended as an imaging position from a third imaging direction in a direction perpendicular to the first imaging direction and opposite to the second imaging direction. Thus, the second imaging-range image in the second screen can be used to guide a FPD imaging position recommendation range on one side (e.g., the right) in a normal direction, and the third imaging-range image in the third screen can be used to guide a FPD imaging position recommendation range on the other side (e.g., the left) in the normal direction. Furthermore, the third screen is displayed together with the first screen and the second screen, and thus a technician can know a FPD imaging position recommendation range from a number of directions with ease.

(7) In the FPD navigation device according to the aforementioned aspect, the guide screen may further have a fourth screen including a fourth imaging-range image indicating a range of an imaging position of the FPD recommended as an imaging position from a fourth imaging direction inclined against the first imaging direction, the fourth imaging direction being located on a plane including an extending direction of the target blood vessel and the first imaging direction, in addition to the first screen and the second screen.

According to this configuration, the guide screen has a fourth screen including a fourth imaging-range image indicating a range of an imaging position of the FPD recommended as an imaging position from a fourth imaging direction inclined against the first imaging direction, the fourth imaging direction being located on a plane including an extending direction of the target blood vessel and the first imaging direction. Thus, the fourth imaging-range image in the fourth screen can be used to guide a FPD imaging position recommendation range in an oblique direction. Furthermore, the fourth screen is displayed together with the first screen and the second screen, and thus a technician can know a FPD imaging position recommendation range from a number of directions with ease.

(8) An aspect in the present disclosure provides a FPD system. The FPD system includes a FPD (flat panel detector) and the FPD navigation device according to the aforementioned aspect.

According to this configuration, the FPD system including a FPD enables guidance of an imaging position of the FPD recommended for acquiring an image of a target blood vessel.

(9) The FPD system according to the aforementioned aspect further includes an arm to support the FPD and change an imaging position of the FPD, and a control portion to control driving of the arm. The FPD navigation device may send the FPD imaging position recommendation range to the control portion, and the control portion may receive and use the FPD imaging position recommendation range to control driving of the arm.

According to this configuration, the FPD navigation device sends the FPD imaging position recommendation range to the control portion, and the control portion receives and uses the FPD imaging position recommendation range to control driving the arm, thus allowing automatization of operation of the FPD in accordance with the FPD imaging position recommendation range.

The present disclosure can be implemented in various modes, such as an information processing apparatus to output a FPD imaging position recommendation range, a FPD (flat panel detector) having a function to calculate a FPD imaging position recommendation range, and a system including these apparatuses, a computer program to achieve functions of these apparatuses and systems, a server apparatus for distributing the computer program, a non-transitory storage medium storing the computer program, and other forms.

BRIEF DESCRIPTION OF DRAWINGS

FIG. 1 is an explanatory diagram illustrating a configuration of a FPD system.

FIG. 7 illustrates step S32 in the guide process.

DETAILED DESCRIPTION OF EMBODIMENTS

First Embodiment

Figure 2A:
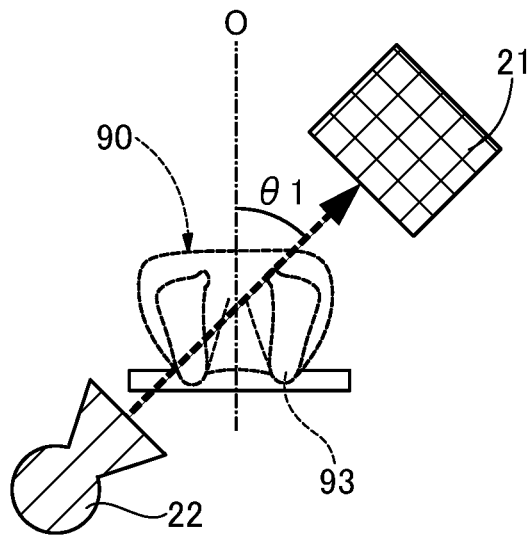
FIGS. 2A to 2D illustrate an imaging position of a first FPD.

FIG. 1 is an explanatory diagram illustrating a configuration of a FPD system 1. The FPD system 1 is a system that acquires an X-ray image of a human body for examination or therapy, and is also referred to as "blood vessel imaging system". The FPD system 1 includes a FPD navigation device 10, a blood vessel imaging apparatus 20 having a FPD (flat panel detector), a display apparatus 30, a table 40, and an operation portion 50. The FPD system 1 according to the embodiment includes the FPD navigation device 10 described later, and thereby enables guidance of a FPD imaging position recommendation range (a range of an imaging position of the FPD recommended for acquiring an image of a target blood vessel) in the blood vessel imaging apparatus 20. Although the term "target blood vessel" means a blood vessel to be targeted for examination or therapy, the FPD system 1 may be used not only for a blood vessel system, but also for a biological lumen such as a lymph gland system, a biliary tract system, a urinary tract system, a respiratory tract system, a digestive organ system, a secretory gland, or a genital organ.

FIG. 1 depicts XYZ-axes perpendicular to one another. The X-axis corresponds to a width direction of the blood vessel imaging apparatus 20, and the Y-axis corresponds to a height direction of the blood vessel imaging apparatus 20, and the Z-axis corresponds to a depth direction of the blood vessel imaging apparatus 20. Hereinafter, a direction to a head 92 of a patient (FIG. 1: human body 90) is also simply referred to as "Z-axis direction", and simply represented as "Z".

The FPD navigation device 10 derives and outputs a FPD imaging position recommendation range in a guide process described later. The FPD navigation device 10 is configured with including a CPU, a ROM, and a RAM, and the CPU executes a computer program stored in the ROM, thereby implementing each function of a main control portion 11, an image acquiring portion 12, a position information acquiring portion 13, and a recommendation range output portion 14. The FPD navigation device 10 is electrically connected to each of a control portion 29, a display apparatus 30, and an operation portion 50 in the blood vessel imaging apparatus 20.

The main control portion 11 sends information to and receives information from the control portion 29, the display apparatus 30, and the operation portion 50 in the blood vessel imaging apparatus 20, and also controls the entirety of the FPD navigation device 10. The main control portion 11 also controls the entirety of a guide process described later.

The image acquiring portion 12 acquires a first image and a second image from the blood vessel imaging apparatus 20 in a guide process. The term "first image" refers to an image including an image of a target blood vessel taken with a FPD located at a freely-selected imaging position. An imaging position of a FPD in acquiring a first image is also referred to as "first position". The term "second image" refers to an image including an image of a target blood vessel taken with a FPD located at a freely-selected imaging position different from a first position. An imaging position of a FPD in acquiring a second image is also referred to as "second position".

The position information acquiring portion 13 acquires position information on a target blood vessel, using a first image, a second image, position information on a FPD in acquiring the first image (i.e., position information on a first position), and position information on a FPD in acquiring the second image (i.e., position information on a second position), in a guide process. Details will be described later.

The recommendation range output portion 14 derives and outputs a FPD imaging position recommendation range (a range of an imaging position of a FPD recommended for acquiring an image of a target blood vessel) from position information on a target blood vessel, in a guide process. The recommendation range output portion 14 in the embodiment generates a guide screen including an image indicating the FPD imaging position recommendation range, and makes a monitor 31 in the display apparatus 30 display the guide screen. Details will be described later.

The blood vessel imaging apparatus 20 has an FPD, and acquires an image by harvesting X-rays transmitted through a human body, and converting them into a digital signal. The blood vessel imaging apparatus 20 has a first FPD 21, a first X-ray tube apparatus 22, a first C arm 23, a first support portion 24, a second FPD 25, a second X-ray tube apparatus 26, a second C arm 27, a second support portion 28, and a control portion 29.

The first FPD 21 includes an X-ray plane detector, converts X-rays entering from the first X-ray tube apparatus 22 into an electrical signal, applies A/D (analogue/digital) conversion, and generates an X-ray image. The first X-ray tube apparatus 22 receives supply of high-voltage power from an X-ray high-voltage apparatus undepicted, and emits an X-ray beam. As indicated by a bold dashed line in the Y-axis direction in FIG. 1, an X-ray beam emitted from the first X-ray tube apparatus 22 enters the first FPD 21 via the human body 90. The first C arm 23 is a C-shaped arm (supporter) that fixes the first FPD 21 and the first X-ray tube apparatus 22 at positions facing each other. The first support portion 24 rotatably supports the first C arm 23. In other words, the first FPD 21 and the first X-ray tube apparatus 22 are fixed at positions facing each other by the first C arm 23 and can move as is to any imaging position around the human body 90 lying on the bed 41. Hereinafter, the first FPD 21 and the first X-ray tube apparatus 22 fixed to the first C arm 23 are also simply referred to as "first FPD 21".

The configuration of the second FPD 25 is similar to that of the first FPD 21. The configuration of the second X-ray tube apparatus 26 is similar to that of the first X-ray tube apparatus 22. As indicated by a bold dashed line in the X-axis direction in FIG. 1, an X-ray beam emitted from the second X-ray tube apparatus 26 enters the second FPD 25 via the human body 90. The second C arm 27 is a C-shaped arm (supporter) that fixes the second FPD 25 and the second X-ray tube apparatus 26 at positions facing each other. The second support portion 28 rotatably supports the second C arm 27. In other words, the second FPD 25 and the second X-ray tube apparatus 26 are fixed at positions facing each other by the second C arm 27 and can move as is to any imaging position around the human body 90. Hereinafter, the second FPD 25 and the second X-ray tube apparatus 26 fixed to the second C arm 27 is also simply referred to as "second FPD 25".

The second FPD 25 is generally disposed in a normal direction of the first FPD 21. For example, when the first FPD 21 is arranged at an imaging position in a front direction of the human body 90 (a vertical direction of the human body 90 and a longitudinal direction of the human body 90) as depicted in FIG. 1, the second FPD 25 is located at an imaging position in a horizontal direction of the human body 90 (a lateral direction of the human body 90). The blood vessel imaging apparatus 20 is sometimes simply referred to as "FPD", or "FPD apparatus".

The control portion 29 is configured with including a CPU, a ROM, and a RAM, and the CPU executes a computer program stored in the ROM, thereby controlling the entirety of the blood vessel imaging apparatus 20. The control portion 29 is electrically connected to each of the first FPD 21, the second FPD 25, the first support portion 24, the second support portion 28, the display apparatus 30, the table 40, and the operation portion 50. The control portion 29 makes the display apparatus 30 display an X-ray image generated by the first FPD 21, the second FPD 25, or another component. In accordance with operation from the operation portion 50, the control portion 29 also drives the first support portion 24 to rotate the first C arm 23, and drives the second support portion 28 to rotate the second C arm 27. Furthermore, in accordance with operation from the operation portion 50, the control portion 29 changes a height of the bed 41 by elongating and contracting an extendable portion 42, and changes a position of the bed 41 by moving the table 40 in the Z-axis direction.

The display apparatus 30 is connected to the FPD navigation device 10, and the control portion 29 in the blood vessel imaging apparatus 20, and functions as an output interface for the FPD navigation device 10 and the blood vessel imaging apparatus 20. The display apparatus 30 has the monitor 31 and an arm 32. The monitor 31 is a "display portion" configured of a well-known means such as a liquid crystal display, Smartglass, or a projector. The arm 32 supports and fixes the monitor 31.

The table 40 is a stand for laying the human body 90 and positioning it close to the first FPD 21 and the second FPD 25. The table 40 has a bed 41, an extendable portion 42, and a leg portion 43. The bed 41 includes a mattress for laying the human body 90. The bed 41 is supported by the table 40 movably in the Z-axis direction. The extendable portion 42 is to elongate and contract in the Y-axis direction, thereby allowing change of a height of the bed 41. The leg portion 43 supports the bed 41 and the extendable portion 42. As indicated by a dashed line in FIG. 1, the human body 90 is laid on the back on the bed 41 with the head 92 placed close to the first FPD 21 and the second FPD 25, and the foot 93 placed far from the first FPD 21 and the second FPD 25. This facilitates acquiring an image of a target blood vessel in a heart 91 by the first FPD 21 and the second FPD 25.

The operation portion 50 is connected to the FPD navigation device 10, and the control portion 29 in the blood vessel imaging apparatus 20, and functions as an input interface for the FPD navigation device 10 and the blood vessel imaging apparatus 20. The operation portion 50 is an "input portion" configured of well-known means such as a touch panel, an operation button, an operation lever, an operation switch, a key board, a mouse, an audio input portion, and a foot switch. In a depicted example, the operation portion 50 is fixed by the table 40.

Figure 2B:
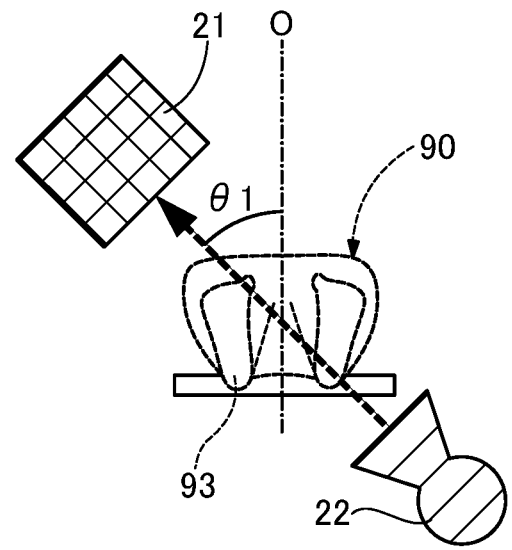
Figure 2C:
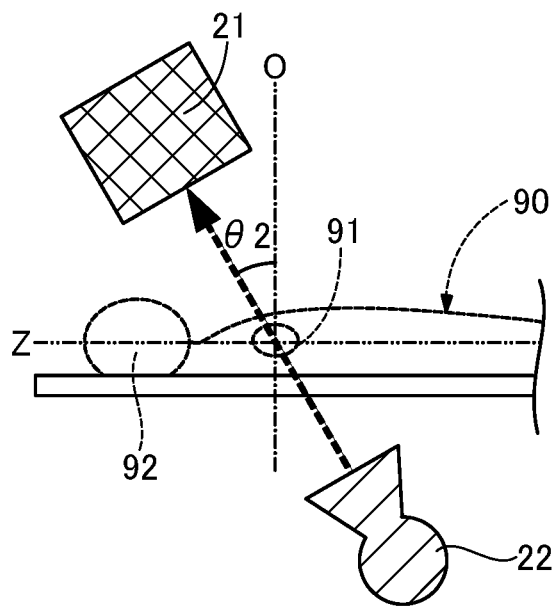
Figure 2D:
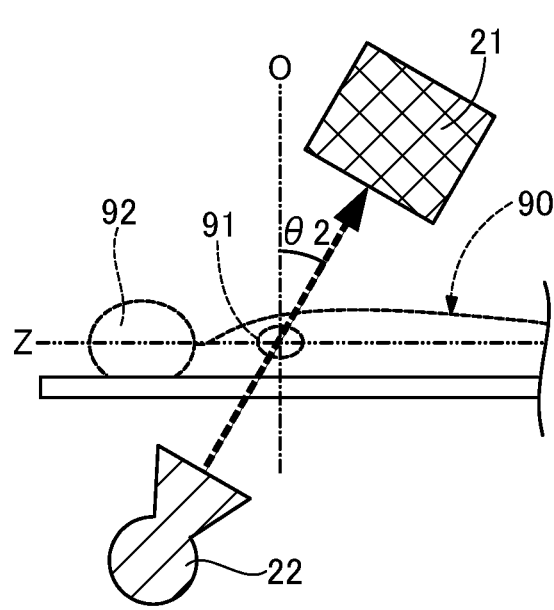

FIGS. 2A to 2D illustrate an imaging position of the first FPD 21. FIG. 2A illustrates LAO, and FIG. 2B illustrates RAO. As depicted in FIG. 2A, positioning the first FPD 21 on the left of the human body 90 is referred to as LAO (left anterior oblique view). As depicted in FIG. 2B, positioning the first FPD 21 on the right of the human body 90 is referred to as RAO (right anterior oblique view). FIG. 2C illustrates CRA, and FIG. 2D illustrates CAU. As depicted in FIG. 2C, positioning the first FPD 21 on the upper of the human body 90 is referred to as CRA (cranial). As depicted in FIG. 2D, positioning the first FPD 21 on the lower of the human body 90 is referred to as CAU (caudal). In other words, "an imaging position of the first FPD 21" is identified by a combination of a right-left position a1 and an upper-lower position a2 as described below:

(a1) classification as LAO or RAO, and an angle $\theta 1$ to a center O of the human body 90, and (a2) classification as CRA or CAU, and an angle $\theta 2$ to the center O of the human body 90.

For example, "RAO28 CRA5" means that the first FPD 21 is located at a position having a 28 degree angle toward the right of the human body 90, and having a 5 degree angle toward the upper of the human body 90.

Figure 3:
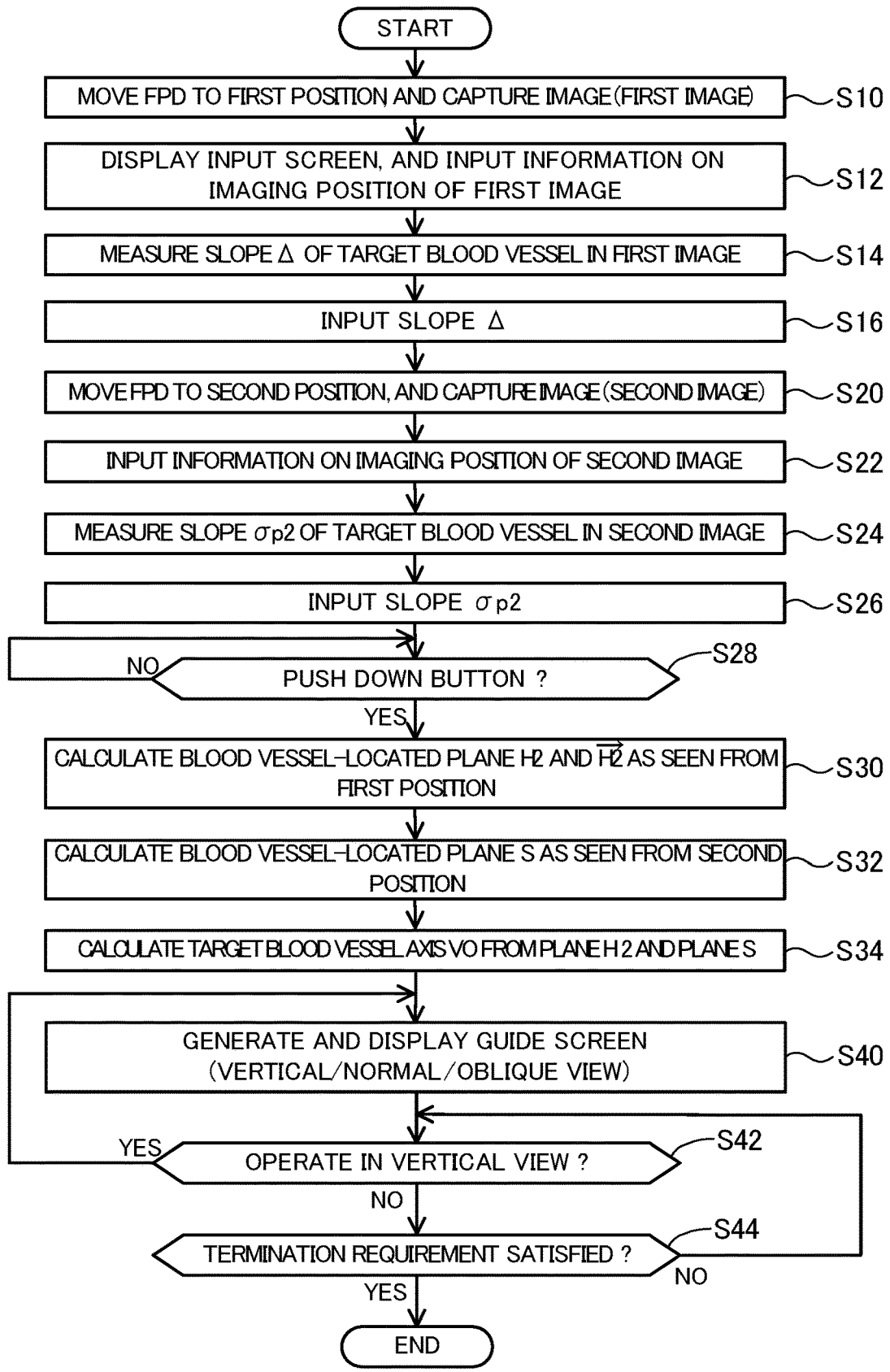
FIG. 3 is a flowchart depicting an exemplary guide process.

FIG. 3 is a flowchart depicting an exemplary guide process. At step S10, the first FPD 21 is moved to a first position, and an X-ray image is taken. The first position can be any position (RAOXX CRAXX: X is an arbitrary natural number). At step S10, imaging may be performed by moving the first FPD 21 to the first position automatically by the main control portion 11 or manually by a technician. The image acquiring portion 12 acquires the taken image (first image) from the blood vessel imaging apparatus 20.

Figure 4:
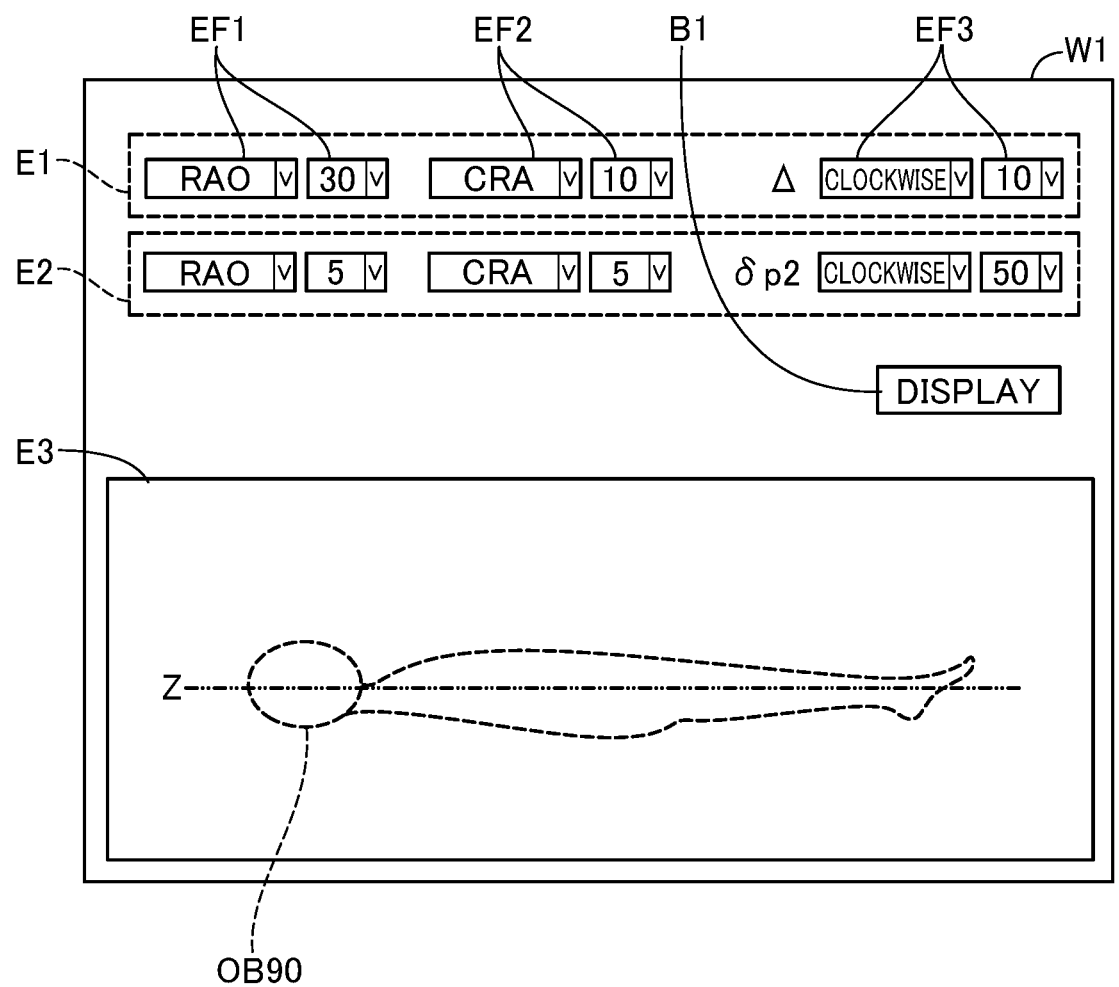
FIG. 4 is an explanatory diagram illustrating an exemplary input screen used in the guide process.

FIG. 4 is an explanatory diagram illustrating an example of an input screen W1 used in the guide process. At step S12 in FIG. 3, the main control portion 11 makes the monitor 31 (display portion) display the input screen W1 depicted in FIG. 4. The input screen W1 is a screen used for inputting and checking position information on the first position and position information on the second position. The input screen W1 includes first image information E1, second image information E2, and a human body image E3, and a display button B1.

The first image information E1 is information on a first image including position information on an imaging position of the first FPD 21 in acquiring the first image (i.e., position information on the first position). The first image information E1 includes an input field EF1, an input field EF2, and an input field EF3. The input field EF1 is used for identifying a right-left position of the first FPD 21 (FIGS. 2A and 2B: LAO/RAO, θ1). The input field EF2 is used for identifying an upper-lower position of the first FPD 21 (FIGS. 2C and 2D: CRA/CAU, θ2). In other words, the input field EF1 and the input field EF2 of the first image information E1 is used for inputting "position information on the first position". The input field EF3 is used for identifying a slope of a target blood vessel.

The second image information E2 is information on a second image including position information on an imaging position of the first FPD 21 in acquiring the second image (i.e., position information on the second position). The second image information E2 includes an input field EF1 for the second position, an input field EF2 for the second position, and an input field EF3 for the second position, in a similar manner as in the first image information E1. In other words, the input field EF1 and the input field EF2 in the second image information E2 is used for inputting "position information on the second position". The human body image E3 displays a model image of the human body 90 lying on the bed 41 and the Z-axis. In an initial state of the input screen W1, all of the input fields EF1-EF3 are blank for each of the first image information E1 and the second image information E2.

Moreover, at step S12, position information on an imaging position of the first FPD 21 in acquiring the first image (position information on the first position) is input for the first image information E1 in the input screen W1. This input may be performed automatically by the main control portion 11 or manually by a technician.

Figure 5A:
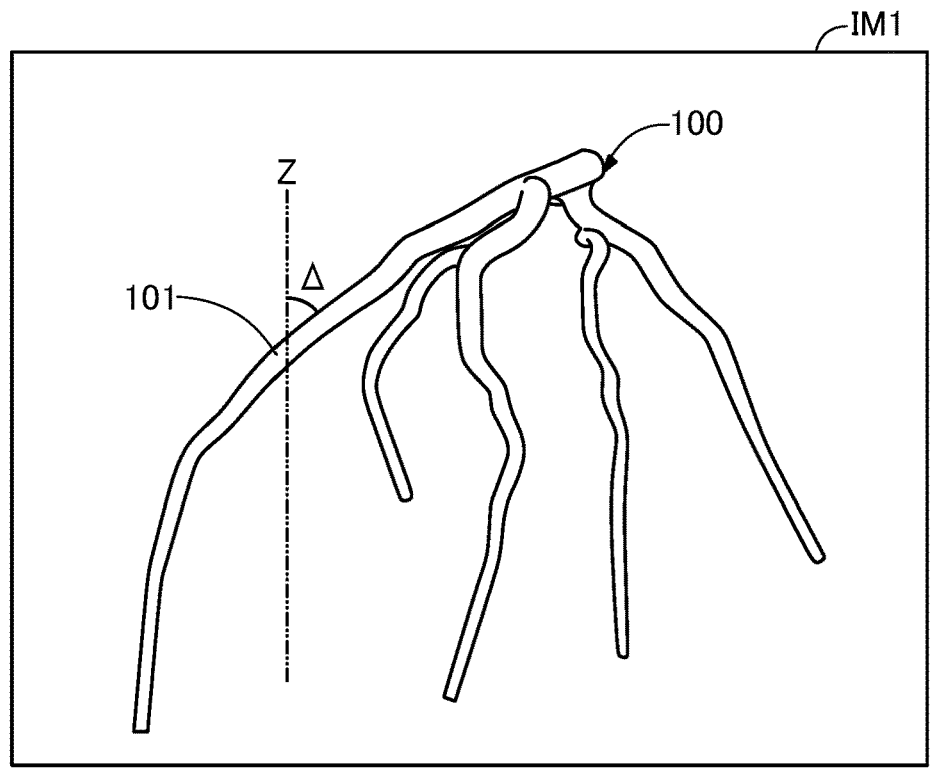
FIGS. 5A and 5B illustrate steps S14 and S24 in the guide process.
Figure 5B:
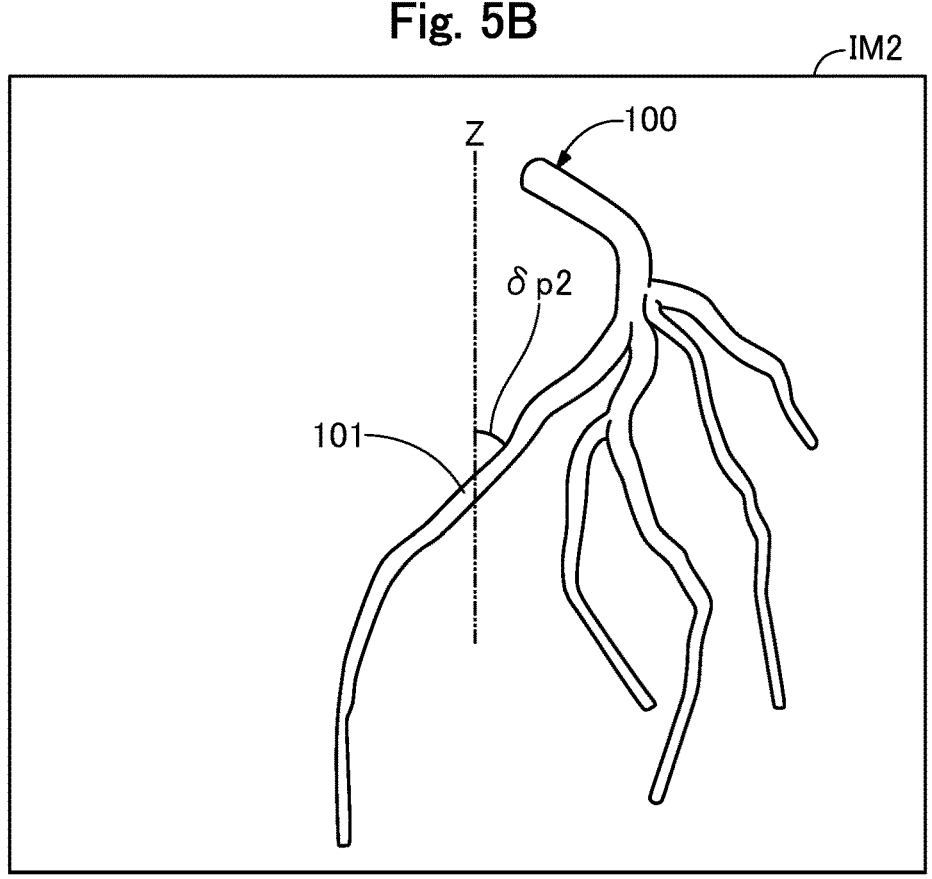

FIGS. 5A and 5B illustrate steps S14 and S24 in the guide process. FIG. 5A illustrates an example of a first image IM1, and FIG. 5B illustrates an example of a second image IM2. At step S14 in FIG. 3, a slope Δ of a target blood vessel in the first image is measured. An exemplary description will be made with illustrating acquisition of the first image IM1 as depicted in FIG. 5A. The first image IM1 includes a coronary artery 100, and a certain branch in the coronary artery 100 is defined as a target blood vessel 101. Then, an angle Δ between the target blood vessel 101 appearing in the first image IM1 and the Z-axis (a direction towards the head 92 of the human body 90) is measured. Measurement of an angle Δ may be performed automatically by the main control portion 11 or manually by a technician, by use of a well-known image processing technique.

At step S16 in FIG. 3, the angle Δ measured at step S14 is input to the input field EF3 of the first image information E1 in the input screen W1. The step S16 may be conducted automatically by the main control portion 11 or manually by a technician.

At step S20, the first FPD 21 is moved to a second position, and an X-ray image is taken. The second position can be any position (RAOYY CRAYY: Y is an arbitrary natural number) different from the first position. At step S20, imaging may be performed by moving the first FPD 21 to the second position automatically by the main control portion 11 or manually by a technician. The image acquiring portion 12 acquires the taken image (second image) from the blood vessel imaging apparatus 20.

At step S22, position information on an imaging position of the first FPD 21 in acquiring the second image (position information on the second position) is input for the second image information E2 in the input screen W1. This input may be performed automatically by the main control portion 11 or manually by a technician.

At step S24, a slope δp2 of a target blood vessel in the second image is measured. An exemplary description will be made with illustrating acquisition of the second image IM2 as depicted in FIG. 5B. An angle δp2 between the target blood vessel 101 appearing in the second image IM2 and the Z-axis (a direction towards the head 92 of the human body 90) is measured. Measurement of an angle δp2 may be performed automatically by the main control portion 11 or manually by a technician by using a well-known image processing technique. Note that the target blood vessel 101 described at step S14 and the target blood vessel 101 described at step S24 mean the same blood vessel.

At step S26 in FIG. 3, the angle δp2 measured at step S24 is input to the input field EF3 of the second image information E2 in the input screen W1. Step S26 may be conducted automatically by the main control portion 11 or manually by a technician.

At step S28, the main control portion 11 determines whether the display button B1 in the input screen W1 is pushed down. If the display button B1 is not pushed down (step S28: NO), the main control portion 11 advances the process to step S28, and stands until the display button B1 is pushed down. If the display button B1 is pushed down (step S28: YES), the position information acquiring portion 13 acquires the first image information E1 and the second image information E2 from the input screen W1, and then advances the process to step S30. Before pushing down the display button B1, a technician may change the first position and reacquire a first image, and may change the second position and reacquire a second image.

Figure 6A:
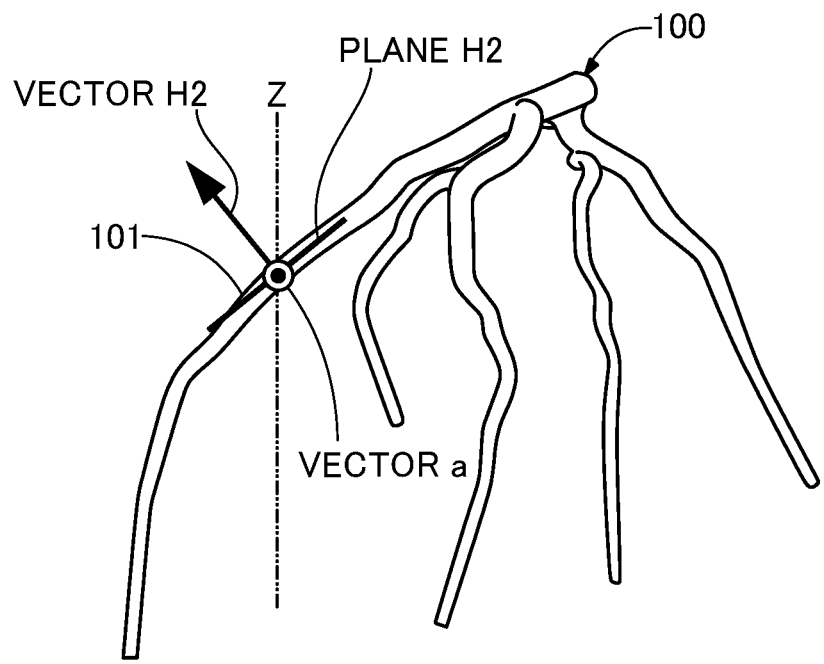
FIGS. 6A and 6B illustrate step S30 in the guide process.
Figure 6B:
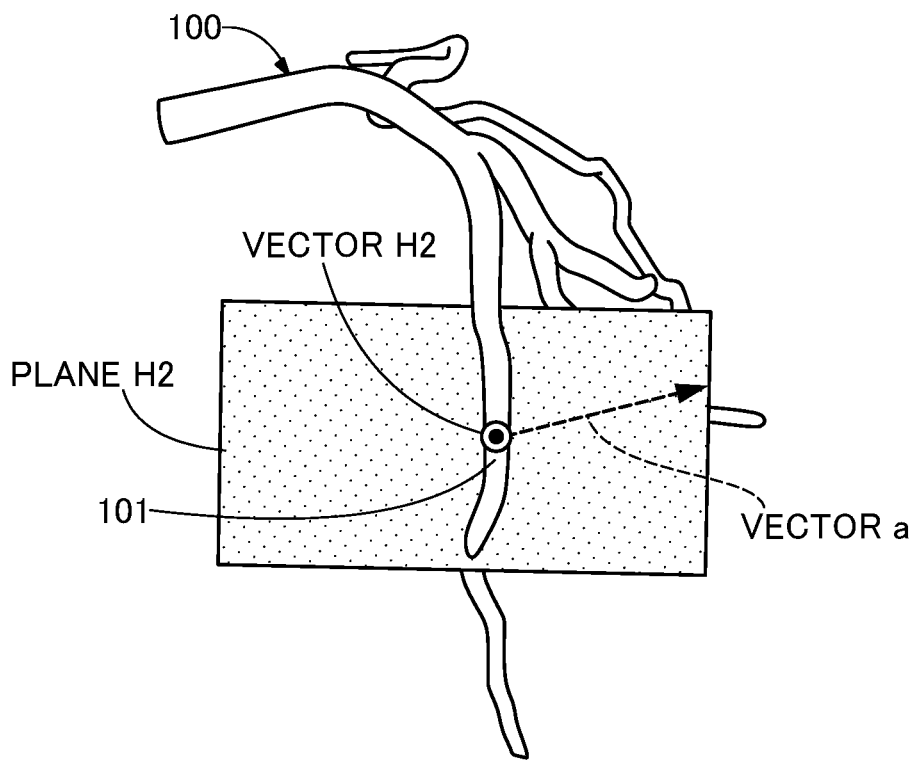

FIGS. 6A and 6B illustrate step S30 in the guide process. FIG. 6A depicts an example of a coronary artery 100 as seen from the same angle as in the first image IM1, and FIG. 6B depicts an example of a coronary artery 100 as seen from an angle different from that in the first image IM1. At step S30 in FIG. 3, the position information acquiring portion 13 calculates a blood vessel-located plane H2 as seen from the first position, and a vector H2. In particular, a viewpoint of the first FPD 21 in the first position (i.e., a normal vector of the first image IM1) is designated as "vector a." The position information acquiring portion 13 defines a plane including a vector a and having the target blood vessel 101 located thereon, and then such a plane is designated as "blood vessel-located plane H2". A blood vessel-located plane H2 is hereinafter also referred to as "plane H2". Additionally, in the position information acquiring portion 13, a normal vector of the plane H2 is referred to as "vector H2".

Figure 8A:
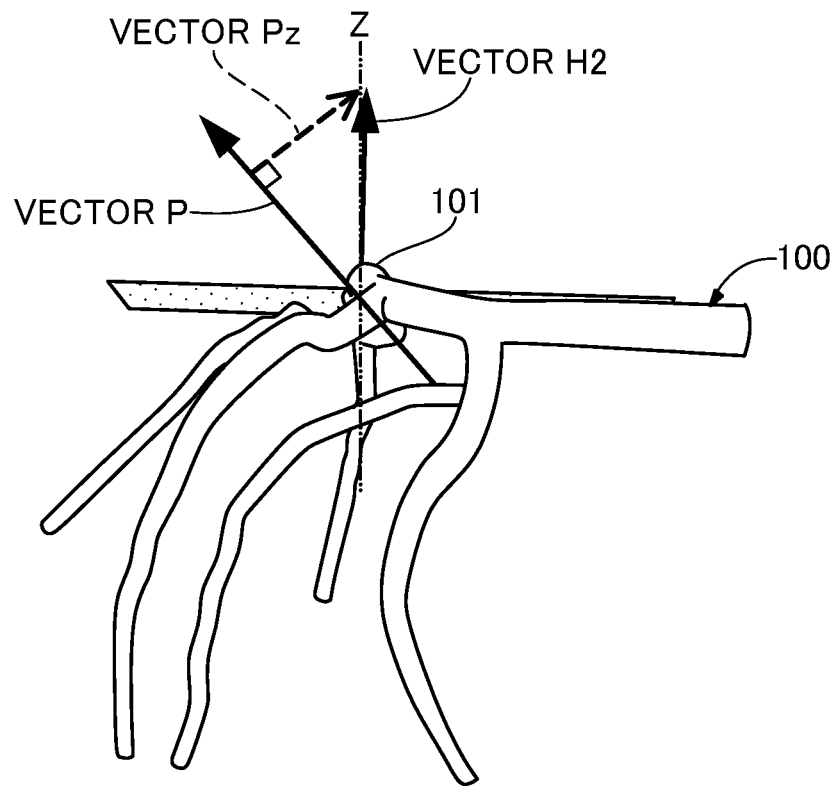
FIGS. 8A and 8B illustrate step S32 in the guide process.
Figure 8B:
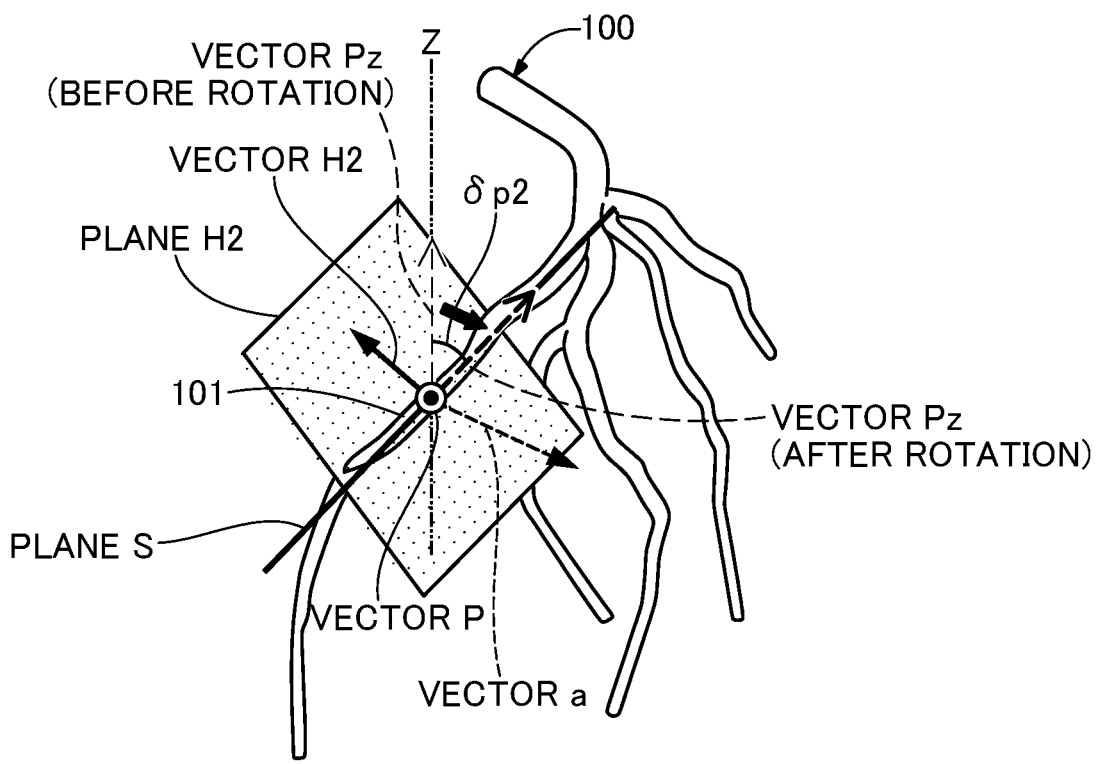

FIG. 7, FIGS. 8A and 8B illustrate step S32 in the guide process. FIG. 7 depicts an example of the coronary artery 100 as seen from the same angle as in the second image IM2, and FIG. 8A and FIG. 8B depict examples of the coronary artery 100 as seen from angles each different from that in the second image IM2. At step S32 in FIG. 3, the position information acquiring portion 13 calculates a blood vessel-located plane S as seen from the second position. In particular, a viewpoint of the first FPD 21 in the second position (i.e., a normal vector of the second image IM2) is designated as "vector P" (FIG. 7). As depicted in FIG. 8A, the position information acquiring portion 13 draws a vector perpendicular to a vector P from the vector P to the Z-axis, and such a vector is designated as "vector Pz". Next, as depicted in FIG. 8B, the position information acquiring portion 13 rotates a vector Pz through an angle of δp2 degree about the vector P. Then, the position information acquiring portion 13 defines a plane between the vector Pz thus rotated and the vector P, and such a plane is designated as "blood vessel-located plane S." A blood vessel-located plane S is hereinafter also referred to as "plane S."

Figure 9A:
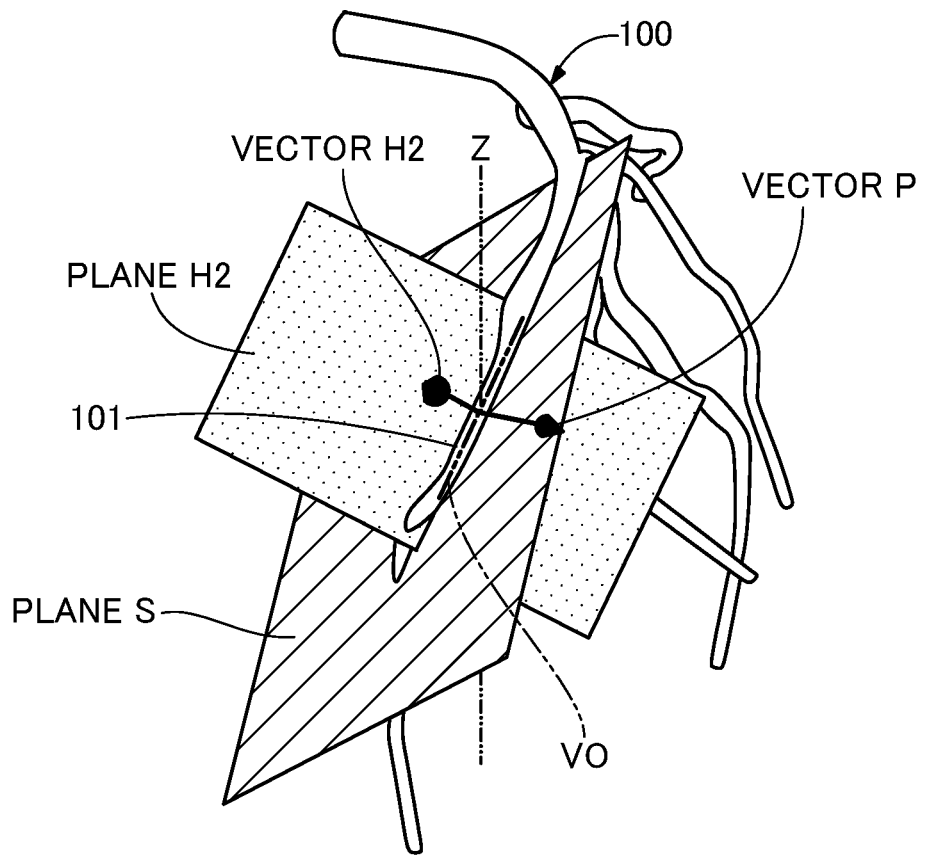
FIGS. 9A and 9B illustrate step S34 in the guide process.
Figure 9B:
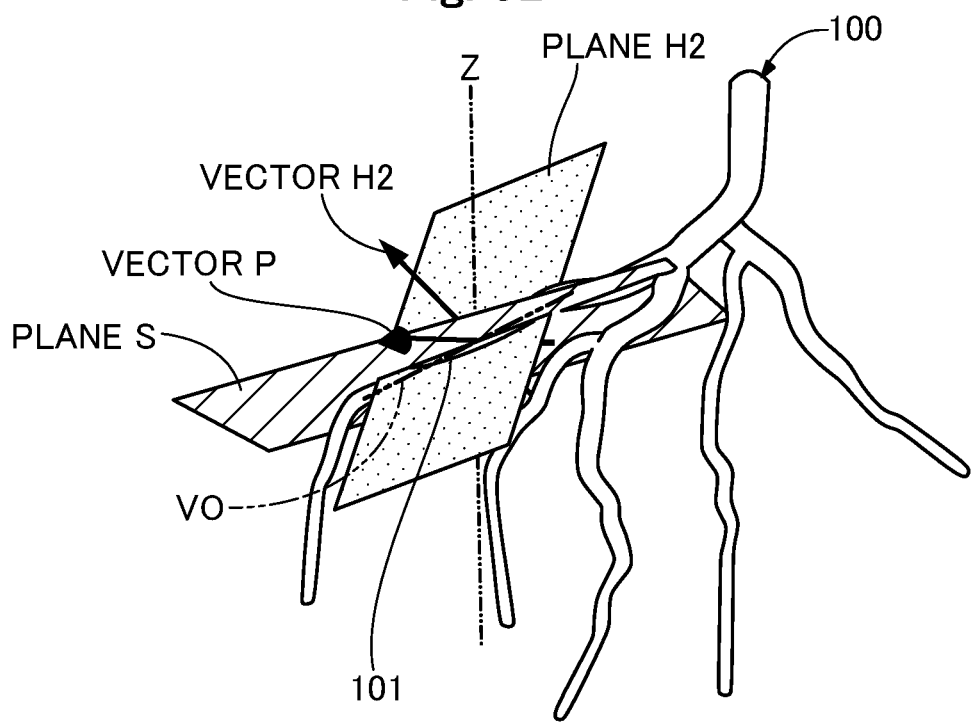

FIGS. 9A and 9B illustrate step S34 in the guide process. FIG. 9A depicts an example of the coronary artery 100 as seen from the same angle as in the second image IM2, and FIG. 9B depicts an example of the coronary artery 100 as seen from an angle different from the second image IM2. FIGS. 9A and 9B depicts the plane H2 with dot hatching, and the plane S with shade hatching. At step S34 in FIG. 3, the position information acquiring portion 13 calculates a target blood vessel axis VO from the plane H2 and the plane S. In particular, the position information acquiring portion 13 defines a straight line where the plane H2 derived at step S30 intersects with the plane S derived at step S32, and such a straight line is designated as "target blood vessel axis VO". A target blood vessel axis VO is hereinafter also referred to as "blood vessel axis vector VO". The blood vessel axis vector VO derived in this manner enables identification of a three-dimensional position of a target blood vessel. The blood vessel axis vector VO corresponds to "position information on a target blood vessel." Steps S30-S34 are substantially the same as solving a problem in that a spatial vector is derived from projected vectors onto two screens.

Figure 10:
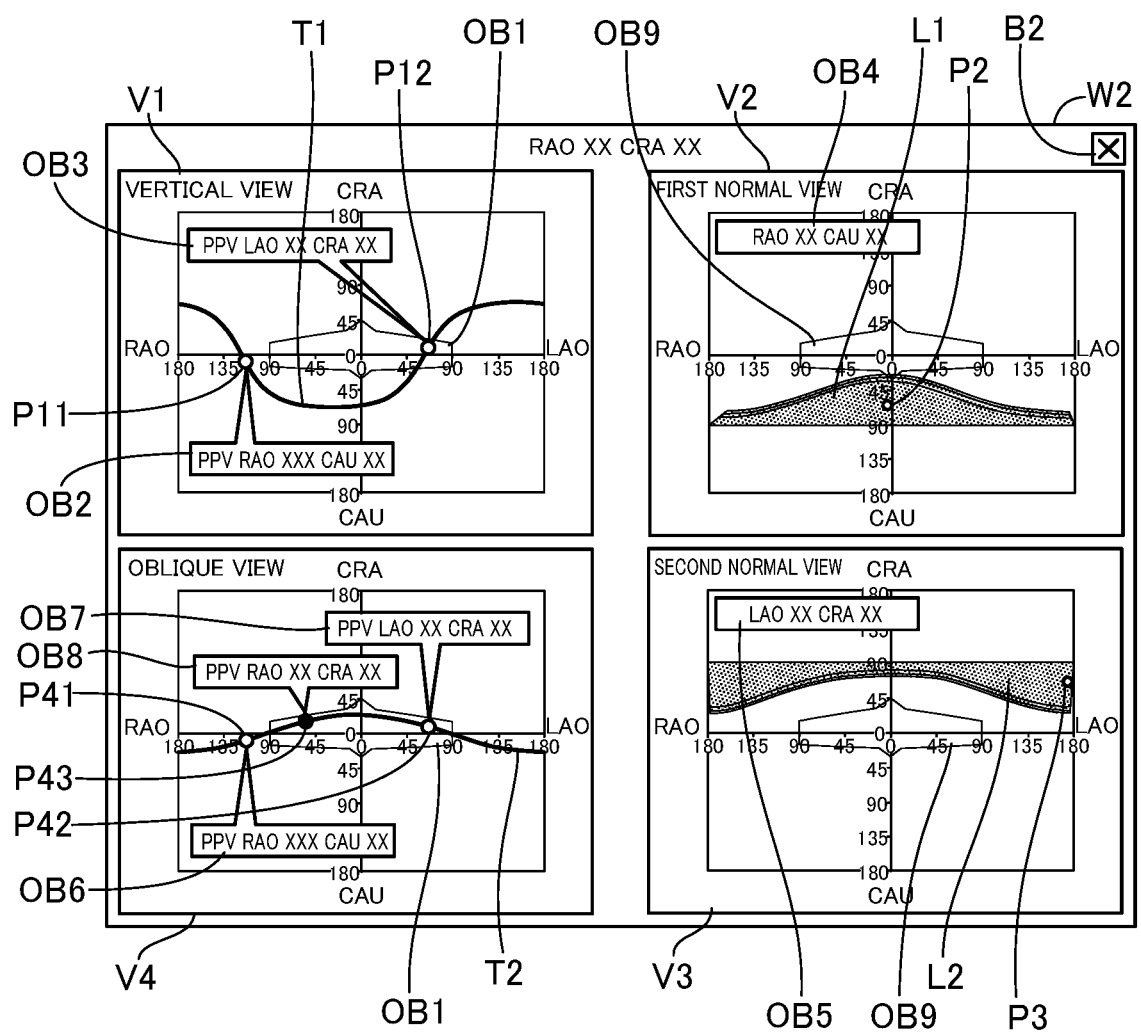
FIG. 10 is an explanatory diagram illustrating an exemplary guide screen in the guide process.

FIG. 10 is an explanatory diagram illustrating an example of a guide screen W2 in the guide process. At step S40 in FIG. 3, the recommendation range output portion 14 generates the guide screen W2 depicted in FIG. 10, and makes the monitor 31 (display portion) display the guide screen W2. The guide screen W2 is a screen used for outputting FPD imaging position recommendation ranges for the first FPD 21 and the second FPD 25 (i.e., a range of an imaging position of the first FPD 21 recommended for acquiring an image of the target blood vessel 101, and a range of an imaging position of the second FPD 25 recommended for acquiring an image of the target blood vessel 101). The guide screen W2 includes a first screen V1, a second screen V2, a third screen V3, and a fourth screen V4. In the embodiment, the first screen V1 is also referred to as "vertical view," the second screen V2 is also referred to as "first normal view," the third screen V3 is also referred to as "second normal view," and the fourth screen V4 is also referred to as "oblique view."

The first screen V1 includes an imaging position range T1, a motion range OB1, an imaging position P11, an imaging position P12, a position indication OB2, and a position indication OB3.

Figure 11:
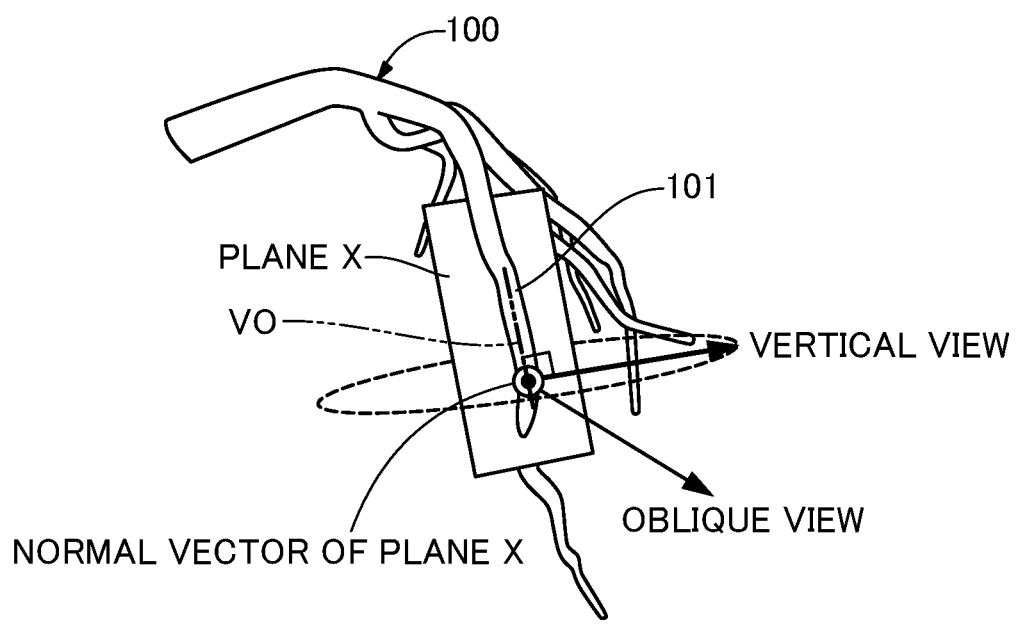
FIG. 11 illustrates an imaging position range.

FIG. 11 illustrates imaging position ranges T1 and T2. The imaging position range T1 and the motion range OB1 are displayed with overlapping onto a background where a right-left position and an upper-lower position of a FPD is indicated in each of the four divided regions and with a scale (FIGS. 2A to 2D: a1, a2). The imaging position range T1 is a curve indicating a range of an imaging position of the first FPD 21 in a direction perpendicular to the blood vessel axis vector VO of the target blood vessel 101 (i.e., an extending direction of the target blood vessel 101) as depicted in FIG. 11. The recommendation range output portion 14 can derive the imaging position range T1 from the blood vessel axis vector VO provided at step S34, using the well-known Rodriguez's rotation formula or other tools. Note that each image provided by the first FPD 21 that moves on the imaging position range T1 is identical to a cross-sectional image of the target blood vessel 101 where a plane X depicted in FIG. 11 is rotated through 360 degrees about the blood vessel axis vector VO. The motion range OB1 is an image indicating a motion range of the first FPD 21 (i.e., a range where the first FPD 21 is actually movable). Within the first screen V1, a part where the imaging position range T1 intersects with the motion range OB1 corresponds to "first imaging-range image", which is a range of an imaging position of the first FPD 21 recommended for acquiring an image of the target blood vessel 101. The first imaging-range image corresponds to "FPD imaging position recommendation range".

The imaging position P11 is a point movable on the imaging position range T1. The imaging position P11 represents a freely-selected imaging position of the first FPD 21 in a direction perpendicular to the blood vessel axis vector VO of the target blood vessel 101. The position indication OB2 indicates a combination of a right-left position and an upper-lower position of the first FPD 21 in the imaging position P11 (FIGS. 2A to 2D: a1, a2). In addition, "X" in the position indication OB2 means an arbitrary natural number. The same is also applied to other portions in FIG. 10. The imaging position P12 is a point that moves on the imaging position range T1 corresponding to movement of the imaging position P11. The imaging position P12 represents an imaging position of the first FPD 21 opposite to the imaging position P11 (reverse direction). The position indication OB3 indicates a combination of a right-left position and an upper-lower position of the first FPD 21 in the imaging position P12 (FIGS. 2A to 2D: a1, a2). The position indications OB2 and OB3 may be omitted.

The second screen V2 includes an imaging position P2, a recommendation range L1, a motion range OB9, and a position indication OB4. The imaging position P2, the recommendation range L1, and the motion range OB9 are displayed with overlapping onto a background where a right-left position and an upper-lower position of a FPD are indicated, as in the first screen V1 (FIGS. 2A to 2D: a1, a2). The imaging position P2 represents an imaging position of the second FPD 25 corresponding to an imaging position of the first FPD 21. In particular, the imaging position P2 represents an imaging position of the second FPD 25 in a direction perpendicular to an imaging direction in the imaging position P11 of the first FPD 21 specified in the first screen V1 (hereinafter also referred to as "first imaging direction") and perpendicular to the blood vessel axis vector VO of the target blood vessel 101. An imaging direction of the imaging position P2 is also referred to as "second imaging direction". The imaging position P2 moves corresponding to movement of the imaging position P11 in the first screen V1. The motion range OB9 is an image indicating a motion range of the second FPD 25 (i.e., a range where the second FPD 25 is actually movable).

The recommendation range L1 corresponds to "second imaging-range image", which is a range of an imaging position of the second FPD 25 recommended for acquiring an image of the target blood vessel 101. The recommendation range L1 is a predetermined range including the imaging position P2, and the size, shape, and another characteristic of the range L1 can be freely determined. In the example in FIG. 10, the recommendation range L1 is displayed as a gradation of a color that changes as close to the motion range OB9. A second imaging-range image corresponds to "FPD imaging position recommendation range". The position indication OB4 indicates a combination of a right-left position and an upper-lower position of the second FPD 25 in the imaging position P2 (FIGS. 2A to 2D: a1, a2). The position indication OB4 may be omitted.

The third screen V3 includes an imaging position P3, a recommendation range L2, the motion range OB9, and a position indication OB5. The imaging position P3, the recommendation range L2, and the motion range OB9 are displayed with overlapping onto a background where a right-left position and an upper-lower position of a FPD are indicated, as in the first screen V1 (FIGS. 2A to 2D: a1, a2). The imaging position P3 represents another imaging position different from the imaging position P2 among imaging positions of the second FPD 25 corresponding to imaging positions of the first FPD 21. In particular, the imaging position P3 represents an imaging position of the second FPD 25 in a direction perpendicular to a first imaging direction of the first FPD 21 and opposite to a second imaging direction of the second FPD 25. An imaging direction of the imaging position P3 is also referred to as "third imaging direction". The imaging position P3 moves corresponding to movement of the imaging position P11 in the first screen V1.

The recommendation range L2 corresponds to "third imaging-range image", which is a range of an imaging position of the second FPD 25 recommended for acquiring an image of the target blood vessel 101. The recommendation range L2 is a predetermined range including the imaging position P3, and the size, shape, and another characteristic of the range L2 can be freely determined. In the example in FIG. 10, the recommendation range L2 is displayed as a gradation of a color that changes as close to the motion range OB9. A third imaging-range image corresponds to "FPD imaging position recommendation range". The position indication OB5 indicates a combination of a right-left position and an upper-lower position of the second FPD 25 in the imaging position P3 (FIGS. 2A to 2D: a1, a2). The position indication OB5 may be omitted.

The fourth screen V4 includes the imaging position range T2, the motion range OB1, an imaging position P41, an imaging position P42, an imaging position P43, a position indication OB6, a position indication OB7, and a position indication OB8. The imaging position range T1 and the motion range OB1 are displayed with overlapping onto a background where a right-left position and an upper-lower position of a FPD are indicated, as in the first screen V1 (FIGS. 2A to 2D: a1, a2). The imaging position range T2 is a curve indicating a range of an imaging position of the first FPD 21 located on a plane including the blood vessel axis vector VO of the target blood vessel 101 (i.e., an extending direction of the target blood vessel 101) and a first imaging direction (FIG. 11: plane X) and inclined against the first imaging direction, as depicted in FIG. 11. Accordingly, the curve of the imaging position range T2 changes corresponding to movement of the first imaging direction (i.e., corresponding to movement of the imaging position P11 in the first screen V1). The recommendation range output portion 14 can derive the imaging position range T2 from the blood vessel axis vector VO provided at step S34, using the well-known Rodriguez's rotation formula or other tools. Within the fourth screen V4, a part where the imaging position range T2 intersects with the motion range OB1 corresponds to "fourth imaging-range image", which is a range of an imaging position of the first FPD 21 recommended for acquiring an image of the target blood vessel 101. The fourth imaging-range image corresponds to "FPD imaging position recommendation range".

The imaging position P41 shows the same point as the imaging position P11, and moves corresponding to movement of the imaging position P11 in the first screen V1. The position indication OB6 displays the same contents as in the position indication OB2. Similarly, the imaging position P42 shows the same point as the imaging position P12, and moves corresponding to movement of the imaging position P12 in the first screen V1. The position indication OB7 displays the same contents as in the position indication OB3. The imaging position P43 is a point capable of being specified at any position on the imaging position range T2. The imaging position P43 represents a freely-selected imaging position of the first FPD 21 located on a plane including the blood vessel axis vector VO of the target blood vessel 101 and a first imaging direction (FIG. 11: plane X) and inclined against the first imaging direction. The position indication OB8 indicates a combination of a right-left position and an upper-lower position of the first FPD 21 in the imaging position P43 (FIGS. 2A to 2D: a1, a2). An imaging direction in the imaging position P43 of the first FPD 21 specified in the fourth screen V4 is also referred to as "fourth imaging direction".

Turning to FIG. 3, description will be continued. At step S42, the recommendation range output portion 14 determines whether operation is made on the first screen V1 (vertical view) in the guide screen W2. In particular, the recommendation range output portion 14 determines whether the imaging position P11 in the first screen V1 is moved. If operated (step S42: YES), the recommendation range output portion 14 advances the process to step S40, updates the first to fourth screens V1-V4 depending on the imaging position P11 thus changed, and makes the monitor 31 display the screens. If not operated (step S42: NO), the recommendation range output portion 14 advances the process to step S44.

At step S44, the recommendation range output portion 14 determines whether a termination requirement is satisfied. The termination requirement can be freely defined; for example, the termination requirement can be determined to be satisfied when a termination button B2 in the guide screen W2 is pushed down. If the termination requirement is not satisfied (step S44: NO), the recommendation range output portion 14 advances the process to step S42 and stands. If the termination requirement is satisfied (step S44: YES), the recommendation range output portion 14 terminates the guide process.

In this manner, in the guide screen W2 in the embodiment, a first imaging-range image in the first screen V1 indicates a range of an imaging position of a FPD recommended as a first imaging position (i.e., as an imaging position of the first FPD 21), and a second imaging-range image in the second screen V2 indicates a range of an imaging position of a FPD recommended as a second imaging position (i.e., as an imaging position of the second FPD 25). Additionally, as described at step S40, the recommendation range output portion 14 displays a second imaging-range image depending on identification of a first imaging position (the imaging position P11 of the first FPD 21). As described at step S42, the recommendation range output portion 14 also changes the second imaging-range image in the second screen V2 corresponding to a first imaging position determined from the first imaging-range image in the first screen V1 (the imaging position P11 of the first FPD 21).

As described so far, according to the FPD navigation device 10 in the first embodiment, the position information acquiring portion 13 can acquire position information on the target blood vessel 101 (blood vessel axis vector VO), using a first image and a second image taken at two different imaging positions (first position and second position), position information on the first position, and position information on the second position (FIG. 3: steps S30-S32). Moreover, the recommendation range output portion 14 derives FPD imaging position recommendation ranges (ranges of imaging positions of the FPDs 21 and 25 recommended for acquiring images of the target blood vessel 101) using the position information on the target blood vessel 101 thus obtained (blood vessel axis vector VO), and outputs the FPD imaging position recommendation ranges. A technician sets imaging positions of the FPDs 21 and 25 so as to overlap the FPD imaging position recommendation ranges thus output, and thereby can guide the FPDs 21 and 25 to appropriate imaging positions. The technician performs a procedure with checking the taken images of the FPDs 21 and 25 obtained in this manner (images of the target blood vessel 101), and thereby can correctly know a positional relation among the blood vessel 101, a lesion, and a medical device, and push and advance the medical device in an intended direction. Consequently, the FPD navigation device 10 in the first embodiment enables guidance of imaging positions of the FPDs 21 and 25 recommended for acquiring images of the target blood vessel 101.

Moreover, according to the FPD navigation device 10 in the first embodiment, the recommendation range output portion 14 makes the monitor 31 (display portion) display the guide screen W2 including an image indicating a FPD imaging position recommendation range, and thus a technician can check the guide screen W2 displayed on the monitor 31, and thereby identify the FPD imaging position recommendation range with ease.

Furthermore, according to the FPD navigation device 10 in the first embodiment, the recommendation range output portion 14 in imaging the target blood vessel 101 at a plurality of imaging positions by the FPDs 21 and 25 may make the guide screen W2 displayed upon identification of a first imaging position, wherein the guide screen W2 includes a second imaging-range image indicating a range of an imaging position of the FPDs recommended as a second imaging position. Thus, for example, the blood vessel imaging apparatus 20 including two FPDs 21 and 25 capable of simultaneous bidirectional imaging such as in a vertical direction (longitudinal direction: first FPD 21) and a normal direction (lateral direction: second FPD 25) enables guidance of a FPD imaging position recommendation range for each of the FPDs 21 and 25.

Furthermore, according to the FPD navigation device 10 in the first embodiment, the recommendation range output portion 14 makes the guide screen W2 displayed, the guide screen W2 having a first screen V1 including a first imaging-range image for a first imaging position (first FPD 21) and a second screen V2 including a second imaging-range image for a second imaging position (second FPD 25), and thus a technician can know a FPD imaging position recommendation range for each of the FPDs 21 and 25 with ease. The recommendation range output portion 14 also changes the second imaging-range image in the second screen V2 corresponding to the first imaging position P11 determined from the first imaging-range image in the first screen V1; thus, for example, the blood vessel imaging apparatus 20 including two FPDs 21 and 25 capable of simultaneous bidirectional imaging such as in a vertical direction (longitudinal direction: first FPD 21) and a normal direction (lateral direction: second FPD 25) enables more appropriate guidance of a FPD imaging position recommendation range for each of the FPDs 21 and 25.

Furthermore, according to the FPD navigation device 10 in the first embodiment, in the guide screen W2, the first imaging-range image in the first screen V1 is indicated as a part having intersection of the range T1 of an imaging position of the first FPD 21 in a direction perpendicular to an extending direction of the target blood vessel 101 (blood vessel axis vector VO) and the motion range OB1 of the first FPD 21. Thus, the first imaging-range image in the first screen V1 can be used to guide a FPD imaging position recommendation range in a vertical direction (longitudinal direction: first FPD 21). Furthermore, in guide screen W2, the second imaging-range image in the second screen V2 is indicated as a predetermined range L1 including the imaging position P2 of the second FPD 25 in a second imaging direction perpendicular to a first imaging direction in the specified imaging position P11 of the first FPD 21 in the first screen V1. Thus, the second imaging-range image in the second screen V2 can be used to guide a FPD imaging position recommendation range in a normal direction (lateral direction: second FPD 25).

Furthermore, according to the FPD navigation device 10 in the first embodiment, the guide screen W2 further has a third screen V3 including a third imaging-range image indicating a range of an imaging position of the second FPD 25 recommended as an imaging position from a third imaging direction in a direction perpendicular to a first imaging direction and opposite to a second imaging direction. Thus, the second imaging-range image in the second screen V2 can be used to guide a FPD imaging position recommendation range on one side (e.g., the right) in a normal direction, and the third imaging-range image in the third screen V3 can be used to guide a FPD imaging position recommendation range on the other side (e.g., the left) in the normal direction. In addition, the third screen V3 is displayed together with the first screen V1 and the second screen V2, and thus a technician can know a FPD imaging position recommendation range from a number of directions with ease.

Furthermore, according to the FPD navigation device 10 in the first embodiment, the guide screen W2 has a fourth screen V4 including a fourth imaging-range image indicating a range of an imaging position of the first FPD 21 recommended as an imaging position from a fourth imaging direction inclined against a first imaging direction, the fourth imaging direction being located on a plane including an extending direction of the target blood vessel 101 (blood vessel axis vector VO) and the first imaging direction. Thus, the fourth imaging-range image in the fourth screen V4 can be used to guide a FPD imaging position recommendation range in an oblique direction. In addition, the fourth screen V4 is displayed together with the first screen V1 and the second screen V2, and thus a technician can know a FPD imaging position recommendation range from a number of directions with ease.

In this way, according to the FPD system 1 in the first embodiment, the FPD system 1 including the FPDs 21 and 25 can guide imaging positions of the FPDs 21 and 25 recommended for acquiring an image of the target blood vessel 101. This allows a technician to correctly know positional relation among the target blood vessel 101, a lesion, and a medical device, and push and advance the medical device in an intended direction. Therefore, in the case of closure inside a blood vessel due to a lesion such as chronic total occlusion (CTO), even a relatively difficult procedure, such as a subintimal approach to re-enter a medical device from a false lumen to a true lumen for opening of CTO (re-opening), can be performed safely and swiftly.

<Other Methods of Deriving a Blood Vessel Axis Vector>

Figure 12:
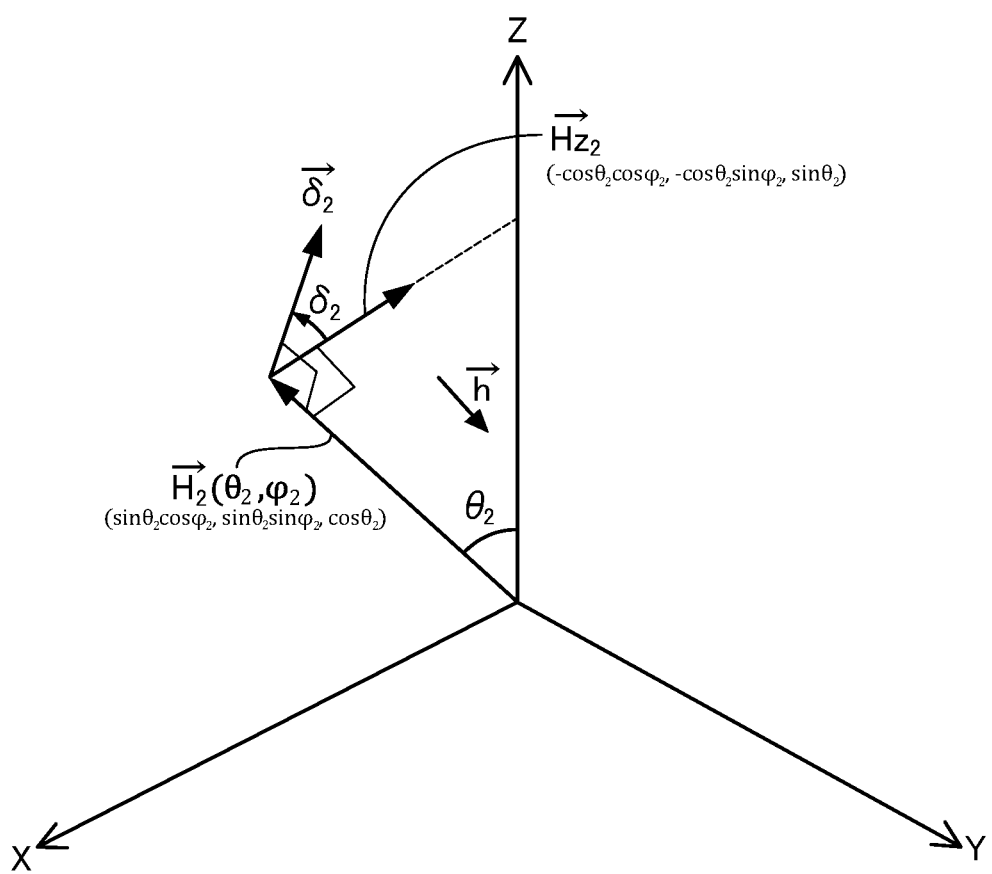
FIG. 12 depicts a relation between a blood vessel axis vector and a plane H2.
Figure 13:
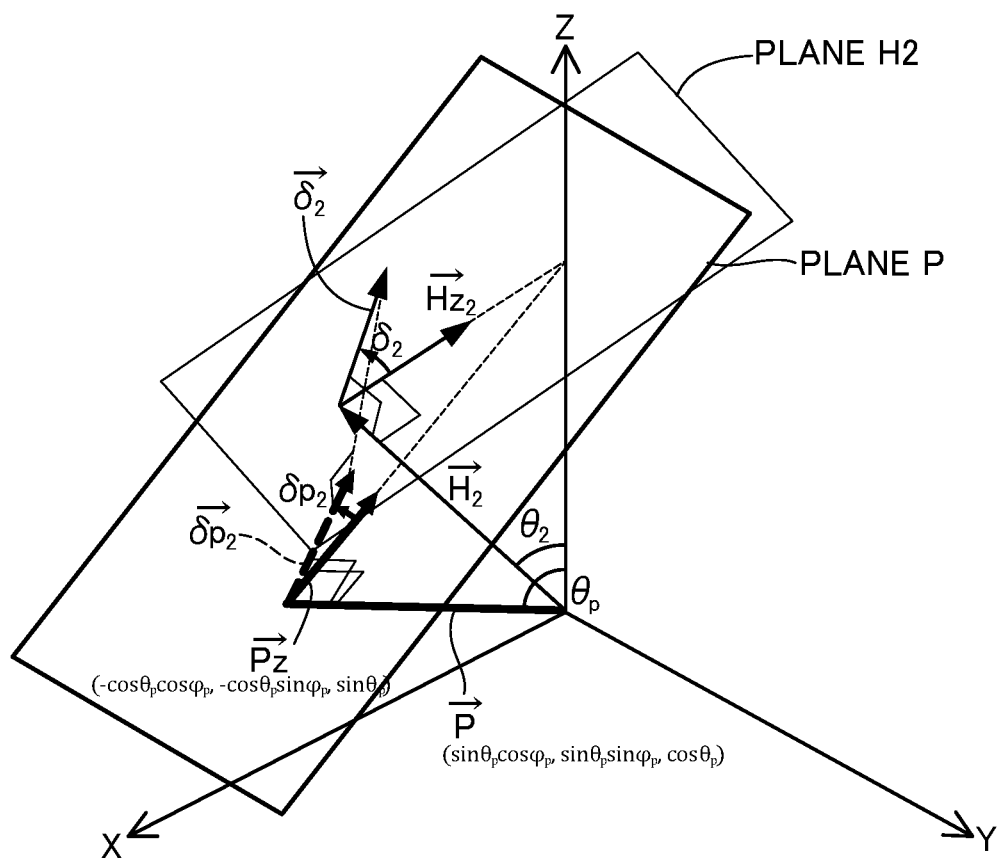
FIG. 13 depicts a relation between the plane H2 and a plane P.
Figure 14:
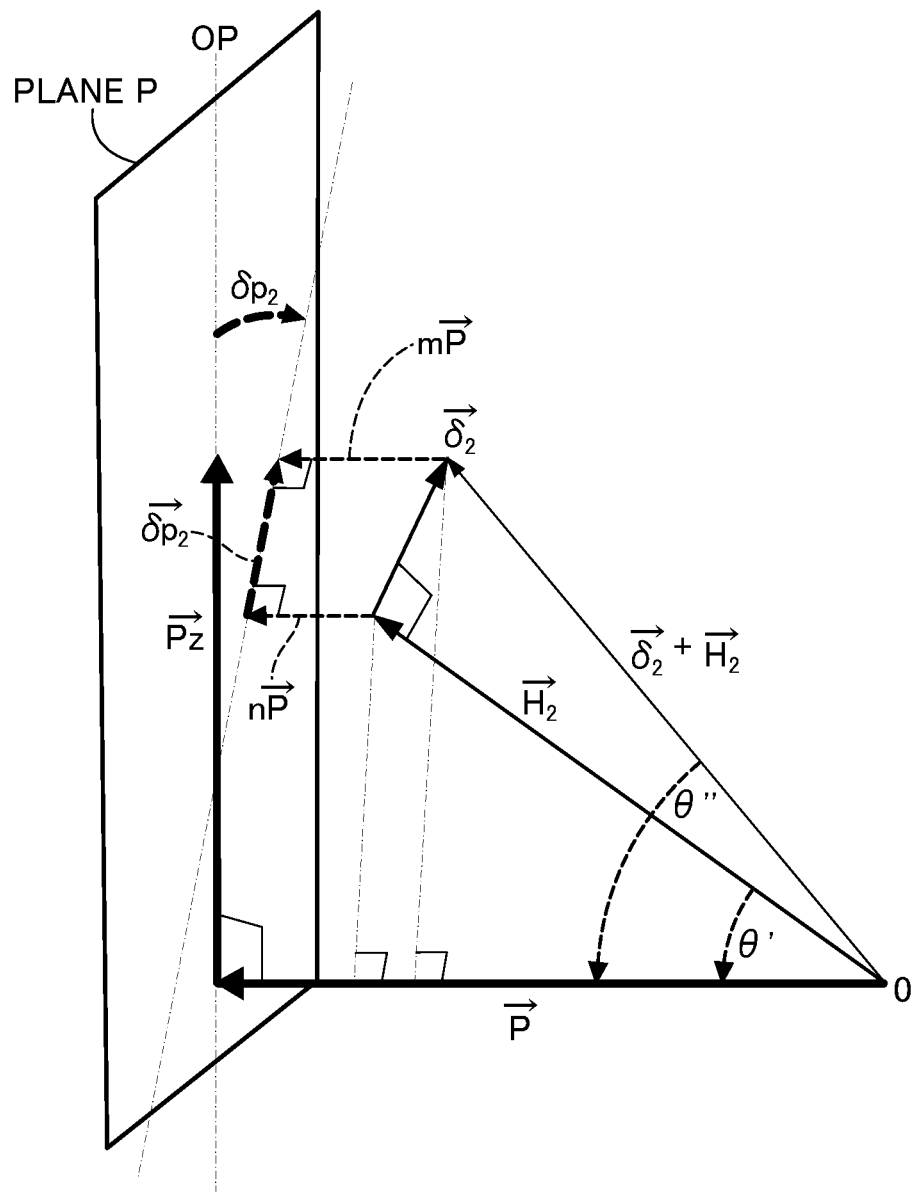
FIG. 14 is an explanatory diagram for calculation of a blood vessel axis vector.

In the guide process in the first embodiment (FIG. 3), the blood vessel axis vector VO described in steps S30 to S34 may be derived by the method illustrated in FIG. 12, FIG. 13, and FIG. 14. Hereinafter, the blood vessel axis vector VO is referred to as "blood vessel axis vector $\delta 2$".

FIG. 12 depicts a relation between a blood vessel axis vector and the plane H2. A vector H2 is a normal vector of the plane H2 (FIGS. 6A and 6B: a blood vessel-located plane as seen from a first position). A vector Hz2 is a unit vector located on the plane H2 and intersecting with the Z-axis (a direction towards the head 92 of the human body 90), overlaps with the Z-axis on the first image, and always directs toward the head 92. A blood vessel axis vector $\delta 2$, which is a calculation target, is derived by rotating the vector Hz2 through an angle of $\delta 2$ degree on the plane H2. The blood vessel axis vector $\delta 2$ can be thus calculated in accordance with the well-known Rodriguez's rotation formula, as the following Formula 1. The symbols $\varphi 2$ and $\theta 2$ in Formula 1 is representation of a polar coordinate of the vector H2. The X,Y-axes depicted in FIG. 12 do not correspond to the X,Y-axes in FIG. 1.

[Formula 1]

$$\vec{\delta_2} = Rn(\delta_2)Hz_2 = \begin{pmatrix} \sin\delta_2\sin\varphi_2 - \cos\theta_2\cos\varphi_2\cos\delta_2 \\ -\sin\delta_2\cos\varphi_2 - \cos\theta_2\sin\varphi_2\cos\delta_2 \\ \sin\theta_2\cos\delta_2 \end{pmatrix} \quad (1)$$

Since the vector Hz2 is vertical to a vector h in FIG. 12, an inner product can be used to calculate a coordinate of the vector Hz2 as shown as Formula 2. Here, the vector h is a normal vector of a plane formed by the vector H2 and the Z-axis.

[Formula 2]

$$(-\cos\theta_2\cos\varphi_2, -\cos\theta_2\sin\varphi_2, \sin\theta_2) \quad (2)$$

FIG. 13 depicts a relation between the plane H2 and a plane P. The plane H2 depicted in FIG. 13 is a blood vessel-located plane as seen from a first position, as illustrated in FIGS. 6A and 6B. The plane P is a projected plane of the first FPD 21 in a second position (i.e., a projected plane of the second image IM2). The vector P is a viewpoint of the first FPD 21 in a second position (i.e., a position vector of the first FPD 21 in the second position, and a normal vector of the plane P). An angle between the blood vessel axis vector $\delta p2$ projected onto the plane P (FIG. 13: dashed line) and a unit vector Pz toward the Z-axis on the plane P is $\delta p2$. Note that the angle $\delta p2$ represents "slope $\delta p2$ of a target blood vessel" measured at step S24 in FIG. 3. The X,Y-axes depicted in FIG. 13 do not correspond to the X,Y-axes in FIG. 1.

The plane P is a plane different from the plane S illustrated in FIG. 7, FIGS. 8A and 8B. The vector Pz is located on the plane P, but is not derived by projecting the vector Hz2 onto the plane P. The blood vessel axis vector $\delta p2$ is derived by projecting the vector $\delta 2$ onto the plane P, is located on the plane P, and intersects with the vector P. Then, an orthogonal coordinate of the vector P is represented as the following Formula 3. In addition, a coordinate of the vector Pz can be calculated as Formula 4. The symbols of $\varphi p$ and $\theta p$ in Formula 3 are representation of a polar coordinate of the vector P.

[Formula 3]

$$(\sin\theta_p \cos\varphi_p, \sin\theta_p \sin\varphi_p, \cos\theta_p) \quad (3)$$

[Formula 4]

$$(-\cos\theta_p \cos\varphi_p, -\cos\theta_p \sin\varphi_p, \sin\theta_p) \quad (4)$$

FIG. 14 is an explanatory diagram for calculation of a blood vessel axis vector. OP in FIG. 14 is a longitudinal median line on the plane P, and intersects with the Z-axis. In FIG. 14, since a vector mP, the vector $\delta 2$+the vector H2, and the vector P are located on the same plane, a relation of Formula 5 is satisfied. Further, since $|\delta 2 + H2| = \sqrt{2}$, a relation of Formula 6 is satisfied for the vector mP and a vector nP.

[Formula 5]

$$m|P| + |\delta_2 + H2|\cos\theta'' = |P| = 1 \quad (5)$$

[Formula 6]

$$m\vec{P} = (1 - \sqrt{2}\cos\theta'')\vec{P}$$

$$n\vec{P} = (1 - \cos\theta'')\vec{P} \quad (6)$$

From Formulas 5 and 6, the blood vessel axis vector $\delta p2$ projected onto the plane P is represented as Formula 7. In addition, an inner product of the vector Pz and the blood vessel axis vector $\delta p2$ projected onto the plane P is represented as Formula 8. Note that the vector Pz and the vector P are orthogonal, and thus gives 0 as the inner product of the vector Pz and the vector P. Therefore, Formula 8 can be transformed to Formula 9.

[Formula 7]

$$\vec{\delta p_2} = \vec{H_2} + \vec{\delta_2} + m\vec{P} - (\vec{H_2} + n\vec{P}) = \vec{\delta_2} + (\cos\theta - \sqrt{2}\cos\theta'')\vec{P} \quad (7)$$

[Formula 8]

$$\vec{Pz} \cdot \vec{\delta p_2} = \vec{Pz} \cdot (\vec{\delta_2} + (\cos\theta' - \sqrt{2}\cos\theta'')\vec{P}) = \vec{Pz} \cdot \vec{\delta_2} + (\cos\theta' - \sqrt{2}\cos\theta'')\vec{Pz} \cdot \vec{P} \quad (8)$$

[Formula 9]

$$\vec{Pz} \cdot \vec{\delta p_2} = \vec{Pz} \cdot \vec{\delta_2} = |\vec{Pz}| |\vec{\delta p_2}| \cos(\delta p_2) = |\vec{\delta p_2}| \cos(\delta p_2) \quad (9)$$

Meanwhile, a right triangle formed by the blood vessel axis vector $\delta p2$ projected onto the plane P, vector(m−n) P and the vector $\delta 2$ gives a relation of Formula 10. Formula 10 leads to a relation of Formula 11. In addition, an inner product of the vector H2 and the vector P is represented by Formula 12. Formula 12 thus leads to a relation of Formula 13 for $\cos\theta'$.

[Formula 10]

$$|\vec{\delta p_2}| = \sqrt{1 - (\cos\theta' - \sqrt{2}\theta'')^2} \quad (10)$$

-continued

[Formula 11]

$$\cos(\delta p_2) = \overrightarrow{Pz} \cdot \overrightarrow{\delta_2} / |\overrightarrow{\delta p_2}| = \left(1 / \sqrt{1-(\cos\theta' - \sqrt{2}\,\theta'')2}\right)\overrightarrow{Pz} \cdot \overrightarrow{\delta_2} \quad (11)$$

[Formula 12]

$$\overrightarrow{H_2} \cdot \overrightarrow{P} = |\overrightarrow{H_2}||\overrightarrow{P}|\cos\theta' = \cos\theta' \quad (12)$$

[Formula 13]

$$\cos\theta' = \begin{pmatrix} \sin\theta_2\cos\varphi_2 \\ \sin\theta_2\sin\varphi_2 \\ \cos\theta_2 \end{pmatrix} \cdot \begin{pmatrix} \sin\theta_p\cos\varphi_p \\ \sin\theta_p\sin\varphi_p \\ \cos\theta_p \end{pmatrix} \quad (13)$$

Also in regard to cos θ″, Formula 14 leads to a relation of Formula 15 in a similar manner as for cos θ′.

[Formula 14]

$$(\overrightarrow{\delta_2} + \overrightarrow{H_2}) \cdot \overrightarrow{P} = |\overrightarrow{\delta_2} + \overrightarrow{H_2}||\overrightarrow{P}|\cos\theta'' = \sqrt{2}\cos\theta'' \quad (14)$$

[Formula 15]

$$\cos\theta'' = 1/\sqrt{2}((\overrightarrow{\delta_2} + \overrightarrow{H_2}) \cdot \overrightarrow{P}) = 1/\sqrt{2}(\overrightarrow{\delta_2} \cdot \overrightarrow{P} + \overrightarrow{H_2} \cdot \overrightarrow{P}) = 1/\sqrt{2}(\overrightarrow{\delta_2} \cdot \overrightarrow{P} + \cos\theta') \quad (15)$$

Then, substituting cos θ′ and cos θ″ into Formula 11 gives Formula 16, and finally provides Formula 17.

[Formula 16]

$$\cos(\delta p_2) = \left(1/\sqrt{1-(\cos\theta' - (\overrightarrow{\delta_2}\cdot\overrightarrow{P} + \cos\theta'))2}\right)\overrightarrow{Pz}\cdot\overrightarrow{\delta_2} = \left(1/\sqrt{1-(\overrightarrow{\delta_2}\cdot\overrightarrow{P})^2}\right)\overrightarrow{Pz}\cdot\overrightarrow{\delta_2} \quad (16)$$

$$\cos^2(\delta p_2)\left(1-(\overrightarrow{\delta_2}\cdot\overrightarrow{P})^2\right) = (\overrightarrow{Pz}\cdot\overrightarrow{\delta_2})^2$$

[Formula 17]

$$\cos^2(\delta p_2)\left(1 - \left(\begin{pmatrix} \sin\delta_2\sin\varphi_2 - \cos\theta_2\cos\varphi_2\cos\delta_2 \\ -\sin\delta_2\cos\varphi_2 - \cos\theta_2\sin\varphi_2\cos\delta_2 \\ \sin\theta_2\cos\delta_2 \end{pmatrix} \cdot \begin{pmatrix} \sin\theta_p\cos\varphi_p \\ \sin\theta_p\sin\varphi_p \\ \cos\theta_p \end{pmatrix}\right)^2\right) =$$

$$\left(\begin{pmatrix} \sin\delta_2\sin\varphi_2 - \cos\theta_2\cos\varphi_2\cos\delta_2 \\ -\sin\delta_2\cos\varphi_2 - \cos\theta_2\sin\varphi_2\cos\delta_2 \\ \sin\theta_2\cos\delta_2 \end{pmatrix} \cdot \begin{pmatrix} -\cos\theta_p\cos\varphi_p \\ -\cos\theta_p\sin\varphi_p \\ \sin\theta_p \end{pmatrix}\right)^2 \quad (17)$$

Then, δp2 in Formula 17 represents "slope δp2 of a target blood vessel" measured at step S24 in FIG. 3. Therefore, the blood vessel axis vector δ2 can be derived by use of Formula 17 and a measurement at step S24. Formula 18 is a solution of the equation represented by Formula 17. The blood vessel axis vector δ2 may be derived by substituting a polar coordinate of the vector H2 (i.e., position information on a first position) and a polar coordinate of the vector P (i.e., position information on a second position) into Formula 18.

[Formula 18]

$$\delta_2 = \tan^{-1}\left\{\pm\sqrt{(r_3^2 - t\alpha^2)/\gamma + \varphi^2/\gamma^2} + \varphi/\gamma\right\} \quad (18)$$

where, $\delta_2 \neq \tan^{-1}\left(\dfrac{t\alpha^2 - r_3}{2\varphi}\right)$, $\delta p_2 \neq \dfrac{\pi}{2}$ $$\begin{bmatrix} r_1 = \sin\theta_p\sin(\varphi_2 - \varphi_p) \\ r_2 = \cos\theta_p\sin(\varphi_2 - \varphi_p) \\ r_3 = \cos\theta_2\sin(\varphi_2 - \varphi_p) \\ \alpha = \cos\theta_p\cos\theta_2\cos(\varphi_2 - \varphi_p) + \sin\theta_p\sin\theta_2 \\ \beta = \sin\theta_p\cos\theta_2\cos(\varphi_2 - \varphi_p) - \cos\theta_p\sin\theta_2 \\ t = \tan^2(\delta p_2) \\ \gamma = r_1^2 + r_2^2 + r_2^2 * t - 1 \\ \varphi = r_1\beta + r_2\alpha + r_2 * \alpha * t \end{bmatrix}$$

Second Embodiment

Figure 15:
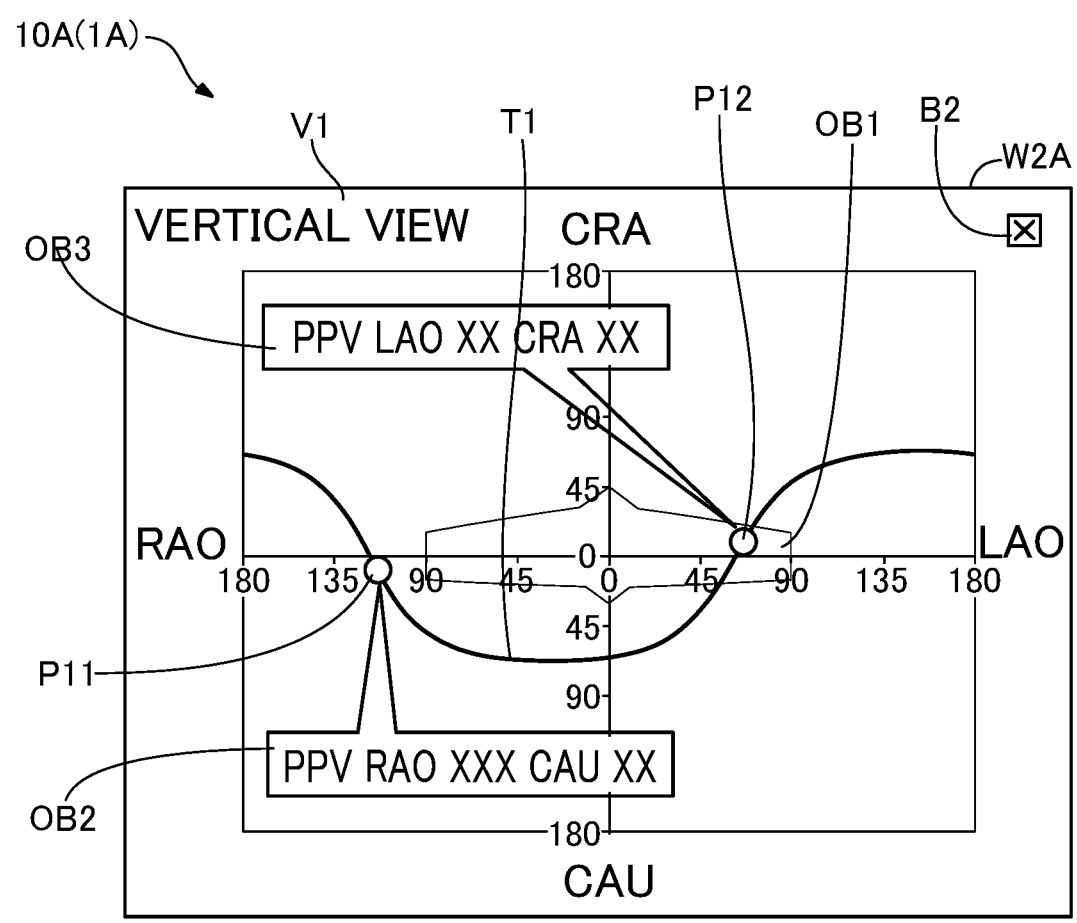
FIG. 15 is an explanatory diagram illustrating an exemplary guide screen in a second embodiment.

FIG. 15 is an explanatory diagram illustrating an example of a guide screen W2A in a second embodiment. In the second embodiment, the FPD system 1A includes a FPD navigation device 10A instead of the FPD navigation device 10. At step S40 in the guide process (FIG. 3), the FPD navigation device 10A generates a guide screen W2A as depicted in FIG. 15 instead of the guide screen W2 illustrated in FIG. 10, and makes the monitor 31 display the guide screen W2A. The guide screen W2A only has the first screen V1, and does not include the second screen V2, the third screen V3, and the fourth screen V4 illustrated in FIG. 10. The FPD navigation device 10A does not also execute step S42 in the guide process.

In this way, the guide screen W2A can have various changes, and may be employed without including the guide screen W2, the third screen V3, and the fourth screen V4. In addition, the first screen V1 may not include at least a part of the imaging position range T1, the motion range OB1, the imaging position P11, the imaging position P12, the position indication OB2, and the position indication OB3, all of which are illustrated in FIG. 10. Such a FPD navigation device 10A according to the second embodiment can also provide an effect similar to that in the first embodiment described above. Incidentally, in the FPD navigation device 10A in the second embodiment, less amount of information in the guide screen W2A allows simple configuration of the guide screen W2A.

Third Embodiment

Figure 16:
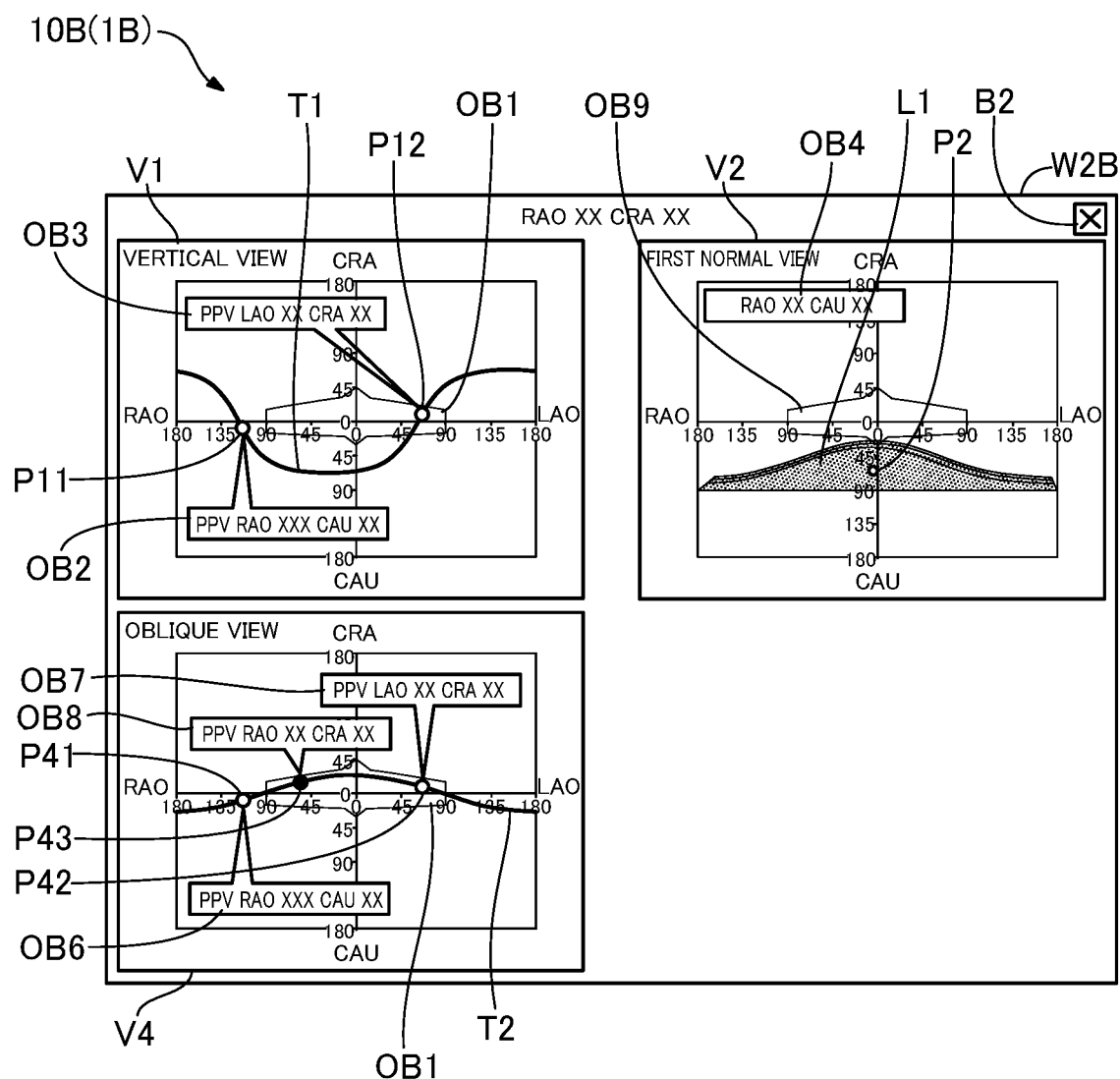
FIG. 16 is an explanatory diagram illustrating an exemplary guide screen in a third embodiment.

FIG. 16 is an explanatory diagram illustrating an example of a guide screen W2B in a third embodiment. In the third embodiment, the FPD system 1B includes a FPD navigation device 10B instead of the FPD navigation device 10. At step S40 in the guide process (FIG. 3), the FPD navigation device 10B generates a guide screen W2B depicted in FIG. 16 instead of the guide screen W2 illustrated in FIG. 10, and makes the monitor 31 display the guide screen W2B. The guide screen W2B has the first screen V1, the second screen V2, and the fourth screen V4, and does not include the third screen V3 illustrated in FIG. 10.

In this way, the guide screen W2B can have various changes, and may be employed without including the third screen V3. The guide screen W2B may also be employed with including the third screen V3 and without including the second screen V2. Moreover, the second screen V2 may not include at least a part of the imaging position P2, the recommendation range L1, the motion range OB9, and the position indication OB4, all of which are illustrated in FIG. 10. Similarly, the third screen V3 may not include at least a part of the imaging position P3, the recommendation range L2, the motion range OB9, and the position indication OB5, all of which are illustrated in FIG. 10. Similarly, the fourth screen V4 may not include at least a part of the imaging position range T2, the motion range OB1, the imaging position P41, the imaging position P42, the imaging position P43, the position indication OB6, the position indication OB7, and the position indication OB8, all of which are illustrated in FIG. 10. Such a FPD navigation device 10B according to the third embodiment can also provide an effect similar to that in the first embodiment described above.

Fourth Embodiment

Figure 17:
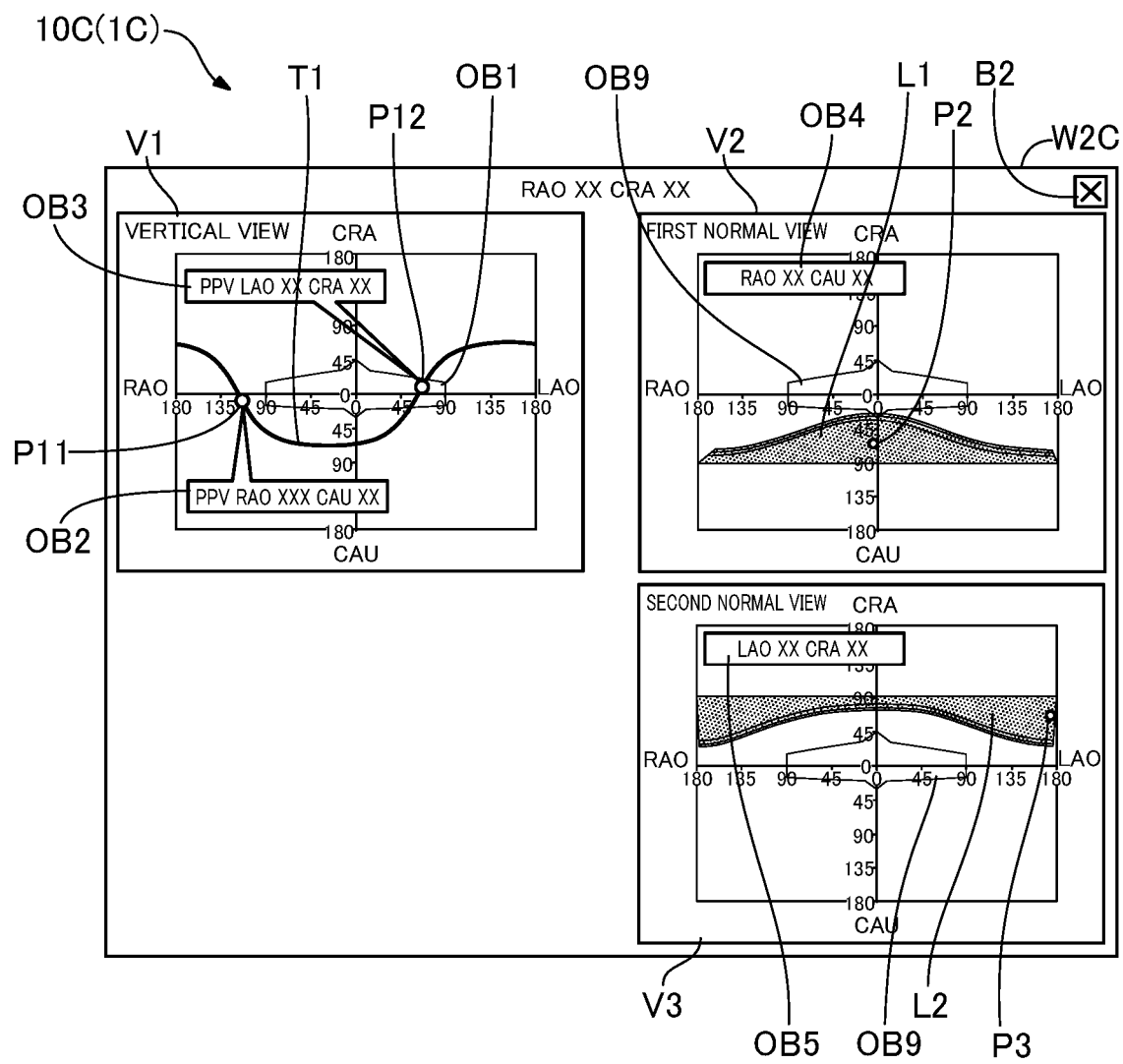
FIG. 17 is an explanatory diagram illustrating an exemplary guide screen in a fourth embodiment.

FIG. 17 is an explanatory diagram illustrating an example of a guide screen W2C in a fourth embodiment. In the fourth embodiment, the FPD system 1C includes a FPD navigation device 10C instead of the FPD navigation device 10. At step S40 in the guide process (FIG. 3), the FPD navigation device 10C generates a guide screen W2C depicted in FIG. 17 instead of the guide screen W2 illustrated in FIG. 10, and makes the monitor 31 display the guide screen W2C. The guide screen W2C has the first screen V1, the second screen V2, and the third screen V3, and does not include the fourth screen V4 illustrated in FIG. 10. In this way, the guide screen W2C can have various changes, and may be employed without including the fourth screen V4. Such a FPD navigation device 10C according to the fourth embodiment can also provide an effect similar to that in the first embodiment described above.

Fifth Embodiment

Figure 18:
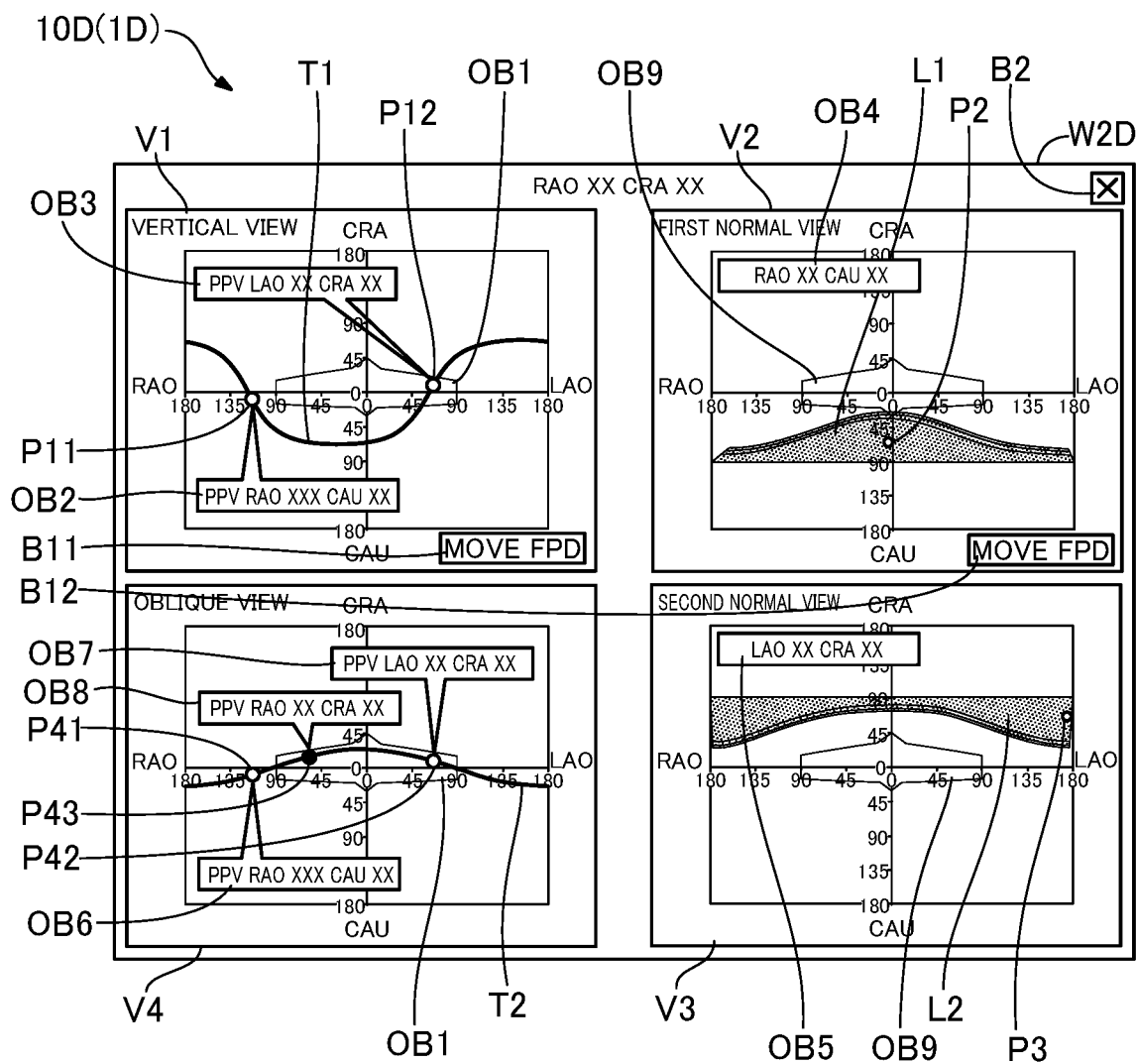
FIG. 18 is an explanatory diagram illustrating an exemplary guide screen in a fifth embodiment.

FIG. 18 is an explanatory diagram illustrating an example of a guide screen W2D in a fifth embodiment. In the fifth embodiment, the FPD system 1D includes a FPD navigation device 10D instead of the FPD navigation device 10. At step S40 in the guide process (FIG. 3), the FPD navigation device 10D generates a guide screen W2D depicted in FIG. 18 instead of the guide screen W2 illustrated in FIG. 10, and makes the monitor 31 display the guide screen W2D.

The guide screen W2D includes the first screen V1, the second screen V2, the third screen V3, and the fourth screen V4, in a similar manner as in the first embodiment. The first screen V1 further includes a FPD moving button B11 in addition to each component described in the first embodiment. Similarly, the second screen V2 further includes a FPD moving button B12 in addition to each component described in the first embodiment. Upon detecting push-down of the FPD moving button B11 at step S40, the main control portion 11 in the FPD navigation device 10D sends information on the imaging position P11 to the control portion 29 of the blood vessel imaging apparatus 20. The control portion 29 drives the first support portion 24 to rotate the first C arm 23, and moves the first FPD 21 to an imaging position represented by the imaging position P11 thus received. Similarly, upon detecting push-down of the FPD moving button B12 at step S40, the main control portion 11 sends information on the imaging position P2 to the control portion 29 of the blood vessel imaging apparatus 20. The control portion 29 drives the second support portion 28 to rotate the second C arm 27, and moves the second FPD 25 to an imaging position represented by the imaging position P2 thus received.

In this way, the guide screen W2D and the guide process can have various changes, and may have a configuration to automatically move an imaging position of the first FPD 21, the second FPD 25, or another FPD to the imaging position P11 or P2 specified. A FPD moving button may be disposed in the third screen V3, the fourth screen V4, or another screen. The position indications OB2, OB3, OB4, OB5, OB6, and OB7 may be omitted. Such a FPD navigation device 10D according to the fifth embodiment can also provide an effect similar to that in the first embodiment described above. The FPD navigation device 10D in the fifth embodiment also allows automatization of operation of the first FPD 21, the second FPD 25, or another FPD, thus providing improved usability of the FPD system 1D.

Sixth Embodiment

Figure 19:
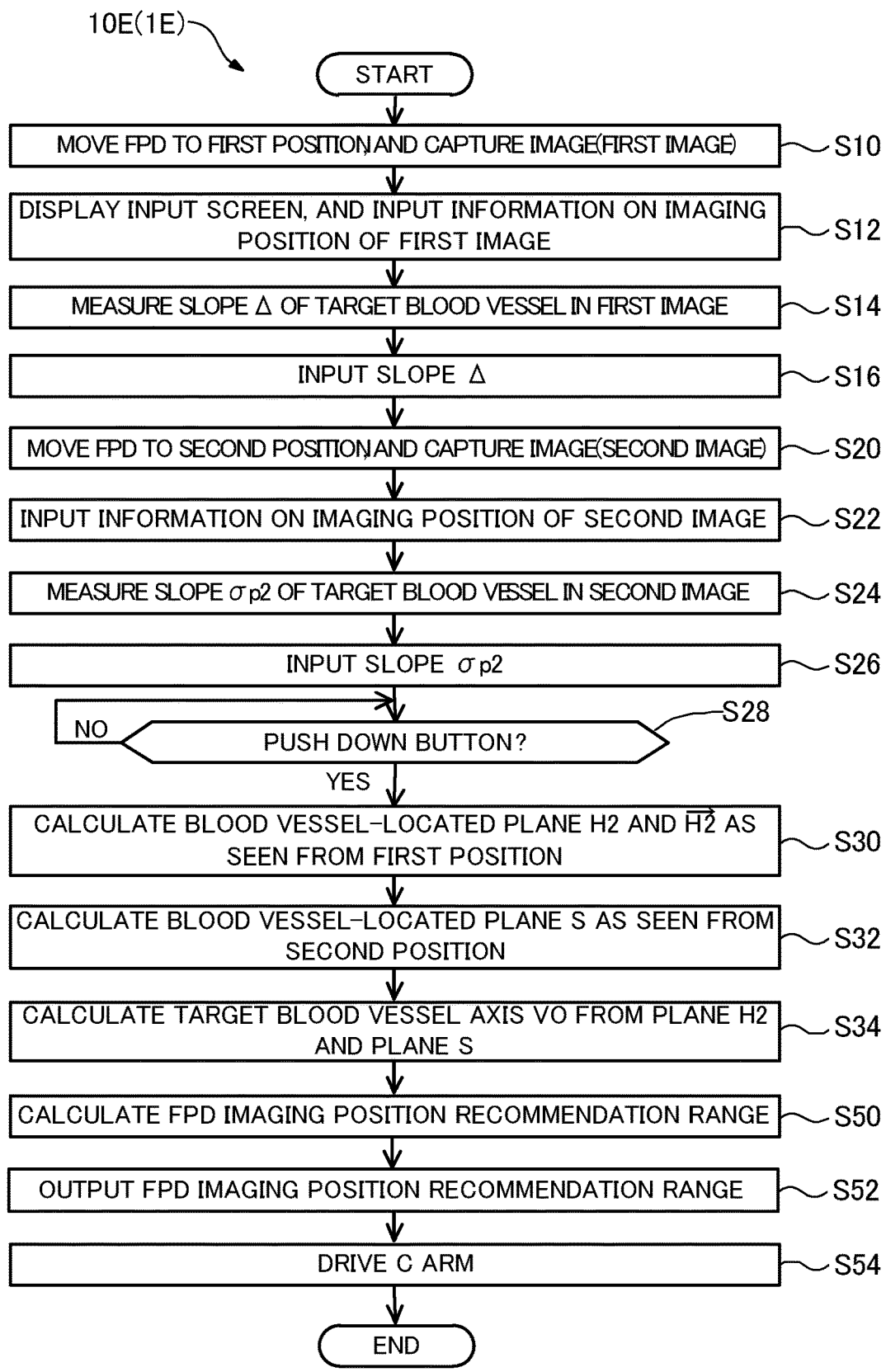
FIG. 19 is a flowchart depicting an exemplary guide process in a sixth embodiment.

FIG. 19 is a flowchart depicting an exemplary guide process in a sixth embodiment. In the sixth embodiment, the FPD system 1E includes a FPD navigation device 10E instead of the FPD navigation device 10. The FPD navigation device 10E executes a guide process provided in FIG. 19, instead of the guide process illustrated in FIG. 3. In the guide process in the sixth embodiment, steps S50-S54 are executed instead of step S40-S44 illustrated in FIG. 3.

At step S50, the recommendation range output portion 14 calculates a FPD imaging position recommendation range from the blood vessel axis vector VO provided at step S34. The FPD imaging position recommendation range can be expressed in various modes. The FPD imaging position recommendation range can be, for example, a candidate for an imaging position of the first FPD 21 where a range of an imaging position of the first FPD 21 in a direction perpendicular to the blood vessel axis vector VO overlaps with a motion range of the first FPD 21 (the candidate may be one or more).

At step S52, the recommendation range output portion 14 outputs (sends) the FPD imaging position recommendation range thus calculated to the control portion 29 in the blood vessel imaging apparatus 20. At step S54, the control portion 29 in the blood vessel imaging apparatus 20 drives the first support portion 24 to rotate the first C arm 23 in accordance with the FPD imaging position recommendation range thus received, and moves the first FPD 21 to an imaging position represented by the FPD imaging position recommendation range thus received. If receiving a plurality of candidates for an imaging position, the control portion 29 selects one imaging position among the plurality of candidates and moves the first FPD 21 to the imaging position by a freely-selected method.

In this way, a guide process can have various changes, and the recommendation range output portion 14 in the FPD navigation device 10E may output a FPD imaging position recommendation range without use of the guide screen W2 illustrated in FIG. 10. The recommendation range output portion 14 may output a FPD imaging position recommendation range of the second FPD 25, instead of a FPD imaging position recommendation range of the first FPD 21, or together with a FPD imaging position recommendation range of the first FPD 21. An output (destination) of a FPD imaging position recommendation range may be an apparatus other than the blood vessel imaging apparatus 20. Such another apparatus may be, e.g., a server apparatus connected via a network or a medical apparatus other than an FPD.

Such a FPD navigation device 10E according to the sixth embodiment can also provide an effect similar to that in the first embodiment described above. Furthermore, the FPD navigation device 10E in the sixth embodiment sends a FPD imaging position recommendation range to the control portion 29 in the blood vessel imaging apparatus 20, and the control portion 29 uses the FPD imaging position recommendation range thus received, to control driving of the first C arm 23 and the first support portion 24 (and the second C arm 27 and the second support portion 28), thus allowing automatization of operation of the first FPD 21 (and the second FPD 25) in accordance with the FPD imaging position recommendation range. This provides improved usability of the FPD system 1E.

Modified Example of the Embodiment

The present disclosure is not limited to the embodiment described above, and can be implemented within a range not departing from the spirit in various modes, and for example, the following variation is also available.

Modified Example 1

In the first to sixth embodiments described above, configurations of the FPD systems 1 and 1A-1E have been described. However, the FPD system 1 can have a configuration with various changes. For example, in the FPD system 1, the FPD navigation device 10 may be connected to the blood vessel imaging apparatus 20 or another component via internet. For example, the display apparatus 30 may be a monitor, a touch panel, or another component built into the FPD navigation device 10. For example, the blood vessel imaging apparatus 20 may have a configuration with a single FPD (i.e., a configuration not including the second FPD 25). For example, the FPD system 1 may have another medical apparatus (e.g., a CT apparatus or an MRI apparatus) or the like not depicted. At that time, the guide screen W2 illustrated in FIG. 10 may include an image acquired by another medical apparatus.

Modified Example 2

In the first to sixth embodiments, configurations of the FPD navigation devices 10 and 10A-10E have been described. However, the FPD navigation device 10 can have a configuration with various changes. For example, a procedure of the guide processes described in FIG. 3, FIG. 19, and other figures may have various change; may change in a performing order of each step, may include omission of at least a part of steps, and may include performing another step undescribed herein.

For example, the image acquiring portion 12 may acquire a first image and a second image via a network, a storage medium, or another tool, rather than from the blood vessel imaging apparatus 20. For example, the position information acquiring portion 13 may use a method different from the method described in FIGS. 5A and 5B to FIGS. 9A and 9B, the method described in FIG. 12 to FIG. 14, or another method, to derive a blood vessel axis vector (position information on a target blood vessel). For example, the position information acquiring portion 13 may derive information other than a blood vessel axis vector (e.g., three-dimensional coordinates of a starting point and an ending point of a target blood vessel) as position information on the target blood vessel. For example, the input screen W1 described in FIG. 4 may not be displayed. For example, within the input screen W1 described in the FIG. 4, at least a part of items may be omitted, and another item may be included.

For example, at step S52 in the guide process in the sixth embodiment (FIG. 19), a FPD imaging position recommendation range may be output by characters or voices instead of outputting a FPD imaging position recommendation range to the blood vessel imaging apparatus 20. In such case, step S54 is omitted. Moreover, step S52 may include outputting a FPD imaging position recommendation range to a simulator or another component in the blood vessel imaging apparatus 20, and simulating operation of an FPD.

Modified Example 3

The configurations of the FPD navigation devices 10, 10A-10E in the first to sixth embodiments may be appropriately combined with each configuration of Modified Examples 1 and 2 described above. For example, the guide screen W2 illustrated in the second to fourth embodiments may include a FPD moving button illustrated in the fifth embodiment.

Although the mode have been described based on the embodiments and modified examples so far, the aforementioned forms for performing the mode are for the purpose of facilitating understanding of the mode, and do not limit the modes. The mode can be changed or modified without departing from the spirit and scope, and the mode also encompasses the equivalent thereof. In addition, the technical characteristics thereof can be appropriately deleted unless described as essential herein.

DESCRIPTION OF REFERENCE NUMERALS 1, 1A-1E: FPD system
10, 10A-10E: FPD navigation device
11: main control portion
12: image acquiring portion
13: position information acquiring portion
14: recommendation range output portion
20: blood vessel imaging apparatus
22: first X-ray tube apparatus
23: first C arm
24: first support portion
26: second X-ray tube apparatus
27: second C arm
28: second support portion
29: control portion
30: display apparatus
31: monitor
32: arm
40: table
41: bed
42: extendable portion
43: leg portion
50: operation portion
90: human body
91: heart
92: head
93: foot
100: coronary artery
101: target blood vessel
B1: display button
B11, B12: FPD moving button
B2: termination button
E1: first image information
E2: second image information
E3: human body image
EF1, EF2, EF3: input field
H2: blood vessel-located plane IM1: first image
IM2: second image
L1, L2: recommendation range
OB1, OB9: motion range
OB2, OB3, OB4, OB5, OB6, OB7, OB8: position indication
P11, P12, P2, P3, P41, P42, P43: imaging position
S: blood vessel-located plane
T1, T2: imaging position range
V1: first screen
V2: second screen
V3: third screen
V4: fourth screen
VO: blood vessel axis vector
W1: input screen
W2, W2A, W2B, W2C, W2D: guide screen

What is claimed is:

1. A FPD navigation device comprising:
a first processor programmed to:
acquire, from a flat panel detector (FPD), a first image of a target blood vessel taken at a first position, and a second image of the target blood vessel taken at a second position different from the first position;
acquire position information on the target blood vessel from the first image, the second image, position information on the first position, and position information on the second position; and
output, from the position information on the target blood vessel, a FPD imaging position recommendation range representing a range of an imaging position of the FPD recommended for imaging the target blood vessel.

2. The FPD navigation device according to claim 1, wherein
the first processor makes a display display a guide screen including an image indicating the FPD imaging position recommendation range.

3. The FPD navigation device according to claim 2, wherein
in imaging the target blood vessel at a plurality of imaging positions by the FPD, and upon identification of a first imaging position, the first processor makes the display display the guide screen that includes a second imaging-range image indicating a range of an imaging position of the FPD recommended as a second imaging position.

4. The FPD navigation device according to claim 3, wherein
the first processor makes the display display the guide screen having:
a first screen including a first imaging-range image indicating a range of an imaging position of the FPD recommended as the first imaging position, and
a second screen including the second imaging-range image, and
the first processor changes the second imaging-range in the second screen corresponding to the first imaging position determined from the first imaging-range image in the first screen.

5. The FPD navigation device according to claim 4, wherein
in the guide screen,
the first imaging-range image in the first screen is indicated as a part having intersection of a range of an imaging position of the FPD in a direction perpendicular to an extending direction of the target blood vessel and a motion range of the FPD, and
the second imaging-range image in the second screen is indicated as a predetermined range including an imaging position of the FPD in a second imaging direction perpendicular to a first imaging direction in a specified imaging position of the FPD in the first screen.

6. The FPD navigation device according to claim 5, wherein
the guide screen further includes a third screen including a third imaging-range image indicating a range of an imaging position of the FPD recommended as an imaging position from a third imaging direction in a direction perpendicular to the first imaging direction and opposite to the second imaging direction.

7. The FPD navigation device according to claim 5, wherein
the guide screen further includes a fourth screen including a fourth imaging-range image indicating a range of an imaging position of the FPD recommended as an imaging position from a fourth imaging direction inclined against the first imaging direction, the fourth imaging direction being located on a plane including an extending direction of the target blood vessel and the first imaging direction.

8. A FPD system comprising:
a flat panel detector (FPD); and
the FPD navigation device according to claim 1.

9. The FPD system according to claim 8, further comprising:
an arm to support the FPD and to change an imaging position of the FPD; and
a second processor programmed to control driving of the arm, wherein
the FPD navigation device sends the FPD imaging position recommendation range to the second processor, and
the second processor receives and uses the FPD imaging position recommendation range to control driving of the arm.

10. A FPD navigation method comprising:
an image acquiring step to acquire a first image of a target blood vessel taken at a first position, and a second image of the target blood vessel taken at a second position different from the first position, the first image and the second image having been imaged by a flat panel detector (FPD);
a position information acquiring step to acquire position information on the target blood vessel from the first image, the second image, position information on the first position, and position information on the second position; and
a recommendation range output step to output, from the position information on the target blood vessel, a FPD imaging position recommendation range representing a range of an imaging position of the FPD recommended for imaging the target blood vessel.

11. The FPD navigation method according to claim 10, wherein
the recommendation range output step makes a display display a guide screen including an image indicating the FPD imaging position recommendation range.

12. The FPD navigation method according to claim 11, wherein
in imaging the target blood vessel at a plurality of imaging positions by the FPD, and upon identification of a first imaging position, the recommendation range output step makes the display display the guide screen that includes a second imaging-range image indicating a range of an imaging position of the FPD recommended as a second imaging position.

13. The FPD navigation method according to claim 12, wherein
the recommendation range output step makes the display display the guide screen having:
a first screen including a first imaging-range image indicating a range of an imaging position of the FPD recommended as the first imaging position, and
a second screen including the second imaging-range image, and
the recommendation range output step changes the second imaging-range in the second screen corresponding to the first imaging position determined from the first imaging-range image in the first screen.

14. The FPD navigation method according to claim 13, wherein
in the guide screen,
the first imaging-range image in the first screen is indicated as a part having intersection of a range of an imaging position of the FPD in a direction perpendicular to an extending direction of the target blood vessel and a motion range of the FPD, and
the second imaging-range image in the second screen is indicated as a predetermined range including an imaging position of the FPD in a second imaging direction perpendicular to a first imaging direction in a specified imaging position of the FPD in the first screen.

15. The FPD navigation method according to claim 14, wherein
the guide screen further includes a third screen including a third imaging-range image indicating a range of an imaging position of the FPD recommended as an imaging position from a third imaging direction in a direction perpendicular to the first imaging direction and opposite to the second imaging direction.

16. The FPD navigation method according to claim 14, wherein
the guide screen further includes a fourth screen including a fourth imaging-range image indicating a range of an imaging position of the FPD recommended as an imaging position from a fourth imaging direction inclined against the first imaging direction, the fourth imaging direction being located on a plane including an extending direction of the target blood vessel and the first imaging direction.

17. A non-transitory computer-readable medium storing thereon a program that causes a computer to perform:
an image acquiring step to acquire a first image of a target blood vessel taken at a first position, and a second image of the target blood vessel taken at a second position different from the first position, the first image and the second image having been imaged by a flat panel detector (FPD);
a position information acquiring step to acquire position information on the target blood vessel from the first image, the second image, position information on the first position, and position information on the second position; and
a recommendation range output step to output, from the position information on the target blood vessel, a FPD imaging position recommendation range representing a range of an imaging position of the FPD recommended for imaging the target blood vessel.

18. The non-transitory computer-readable medium according to claim 17, wherein
the recommendation range output step makes a display display a guide screen including an image indicating the FPD imaging position recommendation range.

19. The non-transitory computer-readable medium according to claim 18, wherein
in imaging the target blood vessel at a plurality of imaging positions by the FPD, and upon identification of a first imaging position, the recommendation range output step makes the display display the guide screen that includes a second imaging-range image indicating a range of an imaging position of the FPD recommended as a second imaging position.

20. The non-transitory computer-readable medium according to claim 19, wherein
the recommendation range output step makes the display display the guide screen having:
a first screen including a first imaging-range image indicating a range of an imaging position of the FPD recommended as the first imaging position, and
a second screen including the second imaging-range image, and
the recommendation range output step changes the second imaging-range in the second screen corresponding to the first imaging position determined from the first imaging-range image in the first screen.

21. The non-transitory computer-readable medium according to claim 20, wherein
in the guide screen,
the first imaging-range image in the first screen is indicated as a part having intersection of a range of an imaging position of the FPD in a direction perpendicular to an extending direction of the target blood vessel and a motion range of the FPD, and
the second imaging-range image in the second screen is indicated as a predetermined range including an imaging position of the FPD in a second imaging direction perpendicular to a first imaging direction in a specified imaging position of the FPD in the first screen.

22. The non-transitory computer-readable medium according to claim 21, wherein
the guide screen further includes a third screen including a third imaging-range image indicating a range of an imaging position of the FPD recommended as an imaging position from a third imaging direction in a direction perpendicular to the first imaging direction and opposite to the second imaging direction.

23. The non-transitory computer-readable medium according to claim 21, wherein
the guide screen further includes a fourth screen including a fourth imaging-range image indicating a range of an imaging position of the FPD recommended as an imaging position from a fourth imaging direction inclined against the first imaging direction, the fourth imaging direction being located on a plane including an extending direction of the target blood vessel and the first imaging direction.

* * * * *